(12) United States Patent
Wang

(10) Patent No.: US 8,986,684 B2
(45) Date of Patent: Mar. 24, 2015

(54) METHODS AND COMPOSITIONS FOR TREATING AUTOIMMUNE DISEASE

(75) Inventor: Yi Wang, Woodbridge, CT (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 74 days.

(21) Appl. No.: 12/452,772

(22) PCT Filed: Jul. 25, 2008

(86) PCT No.: PCT/US2008/009030
§ 371 (c)(1),
(2), (4) Date: Apr. 5, 2010

(87) PCT Pub. No.: WO2009/014744
PCT Pub. Date: Jan. 29, 2009

(65) Prior Publication Data
US 2010/0196374 A1    Aug. 5, 2010

Related U.S. Application Data

(60) Provisional application No. 60/962,044, filed on Jul. 25, 2007.

(51) Int. Cl.
*A61K 39/395*    (2006.01)
*A61K 39/00*    (2006.01)
*C07K 16/00*    (2006.01)
*C07K 16/28*    (2006.01)

(52) U.S. Cl.
CPC .......... *C07K 16/2803* (2013.01); *C07K 2316/96* (2013.01); *A61K 2039/505* (2013.01)
USPC ..................................... 424/130.1; 424/133.1

(58) Field of Classification Search
None
See application file for complete search history.

(56) References Cited

U.S. PATENT DOCUMENTS

| | | | |
|---|---|---|---|
| 3,940,475 A | 2/1976 | Gross | |
| 4,289,747 A | 9/1981 | Chu | |
| 4,376,110 A | 3/1983 | David et al. | |
| 5,223,409 A | 6/1993 | Ladner et al. | |
| 5,225,539 A | 7/1993 | Winter et al. | |
| 5,403,484 A | 4/1995 | Ladner et al. | |
| 5,427,908 A | 6/1995 | Dower et al. | |
| 5,434,131 A | 7/1995 | Linsley et al. | |
| 5,508,717 A | 4/1996 | Miller | |
| 5,530,101 A | 6/1996 | Queen et al. | |
| 5,571,698 A | 11/1996 | Ladner et al. | |
| 5,580,717 A | 12/1996 | Dower et al. | |
| 5,780,279 A | 7/1998 | Matthews et al. | |
| 5,859,205 A | 1/1999 | Adair et al. | |
| 5,902,583 A | 5/1999 | Buchsbaum et al. | |
| 5,916,560 A | 6/1999 | Larsen et al. | |
| 6,011,138 A | 1/2000 | Reff et al. | |
| 6,040,136 A | 3/2000 | Garrard et al. | |
| 6,338,851 B1 | 1/2002 | Gorczynski | |
| 6,632,927 B2 | 10/2003 | Adair et al. | |
| 6,652,858 B2 | 11/2003 | Gorczynski et al. | |
| 6,737,056 B1 | 5/2004 | Presta | |
| 6,749,854 B2 | 6/2004 | Gorczynski et al. | |
| 6,955,811 B2 | 10/2005 | Gorczynski et al. | |
| 6,984,625 B2 | 1/2006 | Gorczynski | |
| 7,238,352 B2 | 7/2007 | Gorczynski et al. | |
| 7,368,535 B2 | 5/2008 | Gorczynski et al. | |
| 7,435,412 B2 | 10/2008 | Bowdish et al. | |
| 7,452,536 B2 | 11/2008 | Gorczynski et al. | |
| 7,887,798 B2 | 2/2011 | Gorczynski et al. | |
| 8,114,403 B2 | 2/2012 | Bowdish et al. | |
| 2002/0031515 A1 | 3/2002 | Caligiuri et al. | |
| 2002/0168364 A1 | 11/2002 | Gorczynski et al. | |
| 2002/0192215 A1 | 12/2002 | Hoek et al. | |
| 2003/0017491 A1 | 1/2003 | Shi et al. | |
| 2004/0018972 A1 | 1/2004 | Gorczynski et al. | |
| 2004/0054145 A1 | 3/2004 | Gorczynski | |
| 2004/0175692 A1 | 9/2004 | Bowdish et al. | |
| 2004/0198661 A1 | 10/2004 | Bowdish et al. | |
| 2005/0048069 A1 | 3/2005 | Gorczynski et al. | |
| 2005/0129690 A1 | 6/2005 | Bowdish et al. | |
| 2005/0169870 A1 | 8/2005 | Truitt et al. | |
| 2006/0024231 A1 | 2/2006 | Schnitzer et al. | |
| 2007/0036786 A1* | 2/2007 | Tuaillon et al. ............. | 424/144.1 |
| 2007/0065438 A1* | 3/2007 | Liversidge et al. ........ | 424/144.1 |
| 2008/0131428 A1 | 6/2008 | Young et al. | |
| 2010/0249382 A1* | 9/2010 | Desjarlais et al. ......... | 530/387.3 |

FOREIGN PATENT DOCUMENTS

| | | |
|---|---|---|
| JP | 02-046297 | 2/1990 |
| WO | WO 84/03508 A1 | 9/1984 |
| WO | WO 85/03508 A1 | 8/1985 |
| WO | WO 92/15679 A1 | 9/1992 |

(Continued)

OTHER PUBLICATIONS

Hegen et al., "Utility of animal models for identification of potential therapeutics for rheumatoid arthritis" Ann Rheum Dis 1008; 67: 1505-1515.*

Stuart et al., "Monkeying Around with Collagen Autoimmunity and Arthritis," Laboratory Investigation, vol. 54(1), pp. 1-3 (1986).*

Huang, "Structural chemistry and therapeutic intervention of protein-protein interactions in immune response, human immunodeficiency virus entry, and apoptosis" Pharmacology & Therapeutics 86 (2000), pp. 201-215.*

Rindfleisch et al., "Diagnosis and Management of Rheumatoid Arthritis" American Family Physician (2005), 72(6), pp. 1037-1047.*

(Continued)

*Primary Examiner* — Daniel E Kolker
*Assistant Examiner* — James Rogers
(74) *Attorney, Agent, or Firm* — Nelson Mullins Riley & Scarborough LLP; Jane E. Remillard, Esq.; Christopher L. Frank

(57) ABSTRACT

The disclosure relates to OX-2/CD200 (herein referred to as CD200) antibodies and methods of treating autoimmune disease.

11 Claims, 6 Drawing Sheets

(56) References Cited

FOREIGN PATENT DOCUMENTS

| WO | WO 94/28027 | | 12/1994 |
|----|----|----|----|
| WO | WO 95/18825 | | 7/1995 |
| WO | WO 96/27011 | A1 | 9/1996 |
| WO | WO 96/38557 | | 12/1996 |
| WO | WO 97/08320 | A1 | 3/1997 |
| WO | WO-97/21450 | | 6/1997 |
| WO | WO 98/27230 | | 6/1998 |
| WO | WO 88/06630 | A1 | 9/1998 |
| WO | WO 99/24565 | | 5/1999 |
| WO | WO 01/87336 | | 11/2001 |
| WO | WO 02/11762 | A2 | 2/2002 |
| WO | WO 02/42332 | A2 | 5/2002 |
| WO | WO 02/46227 | A2 | 6/2002 |
| WO | WO 02/059280 | | 8/2002 |
| WO | WO 02/095030 | | 11/2002 |
| WO | WO 03/025202 | A2 | 3/2003 |
| WO | WO 03074679 | A2 * | 9/2003 |
| WO | WO-2004/060295 | A2 | 7/2004 |
| WO | WO 2004/078937 | A2 | 9/2004 |
| WO | WO 2004/078938 | | 9/2004 |
| WO | WO 2005/007809 | | 1/2005 |
| WO | WO 2006/053301 | A2 | 5/2006 |
| WO | WO-2007/084321 | A2 | 7/2007 |

OTHER PUBLICATIONS

Shields et al. "High Resolution Mapping of the Binding Site on Human IgG1 for FcRI, FcRII, FcRIII, and FcRn and Design of IgG1 Variants with Improved Binding to the FcR" 276, No. 9, 2001, pp. 6591-6604.*

Mackay, "Autoimmune Diseases" N Engl J Med, vol. 345, No. 5, 2001, pp. 340-350.*

Hoek et al. "Down-Regulation of the Macrophage Lineage through interaction with OX2 (CD200)", Science, 290, 2000, pp. 1768-1771.*

Ohno et al., "Antigen-binding specificities of antibodies are primarily determined by seven residues of VH," Proc. Natl. Acad. Sci., vol. 82, pp. 2945-2949 (1985).

Pakula and Sauer, "Genetic analysis of protein stability and function," Annu. Rev. Genet., vol. 23, pp. 289-310 (1989).

Panka et al., "Variable region framework differences result in decreased or increased affinity of variant anti-digoxin antibodies," Proc, Natl. Aswcad. Sci. USA, vol. 85:3080-3084 (1988).

Tao et al., "Structural Features of Human Immunoglobulin G that Determine Isotype-specific Differences in Complement Activation," J. Exp. Med., vol. 178, pp. 661-667 (1993).

Gorczynski et al., "Anti-CD200R Ameliorates Collagen-Induced Arthritis in Mice," Clinical Immunology, vol. 104(3), pp. 256-264 (2002).

Gorczynski, R.M., "CD200 and its receptors as targets for immunoregulation," Current Opinion in Investigational Drugs, vol. 6(5), pp. 483-488 (2005).

Hoek et al., "Down-Regulation of the Macrophage Lineage Through Interaction with OX2 (CD200)," Science, vol. 290, pp. 1768-1771 (2000).

Simelyte et al., "CD200-Fc, a Novel Antiarthritic Biologic Agent That Targets Proinflammatory Cytokine Expression in the Joints of Mice With Collagen-Induced Arthritis," Arthritis & Rheumatism, vol. 58(4), pp. 1038-1043 (2008).

Greenwood, J.D. and Clark, M., "Protein Engineering of Antibody Molecules for Prophylactic and Therapeutic Applications in Man," (ed. Clark, M.) Pub. Academic Titles, UK, pp. 4-5 (1993).

Alizadeh et al., "Distinct types of diffuse large B-cell lymphoma identified by gene expression profiling," Nature, 403:503-511(2000).

Auchincloss et al. "Strategies to Induce Tolerance," Transplantation Immunology, Bach and Auchincloss, Eds., Wiley-Liss, New York, Chapter 11, pp. 211-218 (1995).

Bach, "Immunosuppressive therapy of autoimmune diseases," Immunology Today, 14(6)322-326(1993).

Banerjee, D., et al., "Blocking CD200-CD200 receptor axis augments NOS-2 expression and aggravates experimental autoimmune uveoretinitis in Lewis rats," Ocular Immunology and Inflammation, 12(2):115-125 (2004).

Barclay and Ward, "Purification and Chemical Characterisation of Membrane Glycoproteins From Rat Thymocytes and Brain, Recognised by Monoclonal Antibody MRC OX2," European J. Biochemistry, 129:447-458(1982).

Barclay et al.,"CD200 and membrane protein interactions in the control of myeloid cells," Trends in Immunology, 23(6):2002.

Barclay, A.N., "Different reticular elements in rat lymphoid tissue identified by localization of Ia, Thy-1 and MRC OX 2 antigens," Immunology, 44:727-736 (1981).

Barclay, A.N., et al., "Neuronal/Lymphoid Membrane Glycoprotein MRC OX-2 is a Member of the Immunoglobulin Superfamily with a Light-Chain-Like Structure," Biochem. Soc. Symp., 51:149-157 (1985).

Bauvois et al., Constitutive expression of CD26/dipeptidylpepidase IV on peripheral blood B lymphocytes of patients with B chronic lymphocytic leukaemia. British Journal of Cancer, vol. 79, pp. 1042-1048 (1999).

Blazer, B.R., et al., "CD28/B7 Interactions Are Required for Sustaining the Graft-Versus-Leukemia Effect of Delayed Post-Bone Marrow Transplantation Splenocyte Infusion in Murine Recipients of Myeloid or Lymphoid Leukemia Cells," J. Immunol., 159:3460-3473 (1997).

Bodey et al. "Human Cancer Detection and Immunotherapy with Conjugated and Non-Conjugated Monoclonal Antibodies" Anticancer Research 16: 661-674 (1996).

Bohen, S.P., "Variation in gene expression patterns in follicular lymphoma and the response to rituximab," PNAS, 100(4):1926-1930 (2003).

Boon, Thierry., "Toward a Genetic Analysis of Tumor Rejection Antigens," Advances in Cancer Res., 58:177-210 (1992).

Borriello et al., "MRC OX-2 Defines a Novel T Cell Costimulatory Pathway," J. Immunol., 158:4549-4554 (1997).

Borriello, F., et al., "Characterization and localization of Mox2, the gene encoding the murine homolog of the rat MRC OX-2 membrane glycoprotein," Mammalian Genome, 9(2):114-118 (1998).

Broderick et al., "Constitutive Retinal CD200 Expression Regulates Resident Microglia and Activin State of Inflammatory Cells During Experimental Autoimmune Uveoretinitis," Am. J. of Pathology, 161(5):1669-1677 (2002).

Bukovsky, A., et al., "Association of lymphoid cell markers with rat ascitic malignant cells," IRCS Med. Sci., 11:866-867 (1983).

Bukovsky, A., et al., "Association of some cell surface antigens of lymphoid cells and cell surface differentiation antigens with early rat pregnancy," Immunology, 52:631-640 (1984).

Bukovsky, A., et al., "The localization of Thy-1.1, MRC OX 2 and Ia antigens in the rat ovary and follopian tube," Immunology, 48:587-596 (1983).

Bukovsky, A., et al., "The ovarian follicle as a model for the cell-mediated control of tissue growth," Cell Tissue Res., 236:717-724 (1984).

Caldas et al., "Humanization of the anti-CD18 antibody 6.7: an unexpected effect of a framework residue in binding to antigen," Mol. Immunol. 39:941-952 (2003).

Chaouat and Clark, FAS/FAS Ligand Interaction at the Placental Interface is not Required for the Success of Allogeneic Pregnancy in Anti-Paternal MHC Preimmunized Mice, Presented at the 6th Congress of the Adria-Alps Soc. of Immunol. of Reprod., (2000) / Amer. J. of Reprod. Immunol., 45:108-115 (2001).

Chen, D., et al., "Discrete Monoclonal Antibodies Define Functionally Important Epitopes in the CD200 Molecule Responsible for Immunosupression Function," Transplantation, 79:282-288 (2005).

Chen, D., et al., "Synthetic peptides from the N-terminal regionsl of CD200 and CD200R1 modulate immunosupressive and anti-inflammatory effects of CD200-CD200R1 interaction," International Immunology, 17(3):289-296 (2005).

Chen, Z., et al., "Cloning and characterization of the murine homologue of the rat/human MRC OX-2 gene," Database Medline, Biochemica et Biophysica Acta, 1362(1):6-10 (1997).

Cherwinski, H.M., et al., "The CD200 Receptor Is a Novel and Potent Regulator of Murine and Human Mast Cell Function," J. Immunol., 174:1348-1356 (2005).

(56) References Cited

OTHER PUBLICATIONS

Chien et al., "Significant structural and functional change of an antigen-binding site by a distant amino acid substitution: proposal of a structural mechanism," Proc. Natl. Acad. Sci. USA 86:5532-5536 (1989).
Chitnis et al., "The Role of CD200 in Immune-Modulation and Neural Protection in EAE," Abstract, 12th International Congress of Immunology and 4th Annual Conference of FOCIS, Montreal, Jul. 21, 2004.
Chitnis, T., et al., "Elevated Neuronal Expression of CD200 Protects $Wld^s$ Mice from Inflammation-Mediated Neurodegeneration," American Journal of Pathology, 170(5):1695-1712 (2007).
Clark et al., "Fg12 prothrombinase expression in mouse trophoblast and decidua triggers abortion but may be countered by OX-2," Mol. Human Reprod., 7:185-194 (2001).
Clark et al., "Labile CD200 tolerance signal important in transfusion-related immunomodulation (TRIM) prevention of recurrent miscarriages," Amer. J. Reprod. Immunol., 45:361 (2001).
Clark et al., "Procoagulants in fetus rejection: the role of the OX-2 (CD200) tolerance signal," Seminars in Immunol., 13(4)255-263 (2001).
Clark et al., "The OX-2 Tolerance Signal Molecule at the Fetomaternal Interface Determines Pregnancy Outcome," Amer. Journal of Reprod Immunol., 43:326 (2000). Abstract Only.
Clark et al., Amer. Soc. for Reprod. Medicine, 55th Annual Meeting (1999).
Clark, D.A., "Intralipid as Treatment for Recurrent Unexplained Abortion?", Am. J. of Reprod. Immunol., 32:290-293 (1994).
Clark, M.J., et al., "MRC OX-2 antigen: a lymphoid/neuronal membrane glycoprotein with a structure like a single immunoglobulin light chain," EMBO Journal, 4(1):113-118 (1985).
Clarke, M.J., "MRC OX-2 lymphoid brain glycoprotein: S1 mapping suggests higher levels of abnormal RNA in the thymus than in the brain," Biochemical Society Transactions, 14:80-81 (1986).
Cochlovius et al., "Cure of Burkitt's Lymphome in Severe Combined Immunodeficiency Mice by T Cells, Tetravalent CD3 × CD19 Tandem Diabody, and CD28 Costimulation," Cancer Res. 60:4336-4341 (2000).
Cohen, P.L., "Systemic Autoimmunity," in Fundamental Immunology, Fourth edition, W.E. Paul, Editor, Lippincott-Raven Publishers, Philadelphia, Ch. 33, p. 1067-1088 (1999).
DeNardo et al., "Increased Survival Associated with Radiolabeled Lym-1 Therapy for Non-Hodgkin's Lymphoma and Chronic Lymphocyctic Leukemia." Cancer Supplement (1997) vol. 80, No. 12. pp. 2706-2711.
Dennis, C., "Off by a whisker," Nature, 442,:739-741 (2006).
Dick et al., "Control of Myeloid Activity During Retinal Inflammation," J. of Leukocyte Bio., 74:161-166(2003).
Ebert et al., "Selective Immunosuppressive Action of a Factor Produced by Colon Cancer Cells," Cancer Res. 50:6158-6161 (1990).
Elgert, K. D. "Immunology : Understanding the Immune System," The Genetic Basis of Antibody Diversity, 123 (1996).
Faguet et al., "Blood Kinectics, Tissue Distribution, and Radioimaging of Anti-Common Chronic Lymphatic Leukemia Antigen (cCLLa) Monoclonal Antibody $CLL_2$ in Mice Transplanted With cCLLa- Bearing Human Leukemia Cells." Blood. vol. 75, No. 9 (1990) pp. 1853-1861.
Faisal et al., Cell-surface Associated p43/Endothelial-monocyte-activating-polypeptide-II in Hepatocellular Carcinoma Cells Induces Apoptosis in T-lymphocytes, Asian J. of Surg. 30(1):13-22 (2007).
Fallarino, F., et al., "Murine Plasmacytoid Dendritic Cells Initiate the Immunosupressive Pathway of Tryptophan Catabolism in Response to CD200 Receptor Engagement," J. Immunol., 173:3748-3754 (2004).
Farber, U., et al., "Loss of heterozygosity on chromosome 3, bands q24->qter, in a diploid meningioma," Cytogenet Cell Genet, 57:157-158 (1991).

Feuerstein et al., "Induction of Autoimmunity in a Transgenic Model of B Cell Receptor Peripheral Tolerance: Changes in Coreceptors and B Cell Receptor-Induced Tyrosine-Phosphoproteins," J. Immunol. 163:5287-5297 (1999).
Funakoshi et al., "Antitumor Effects of Nonconjugated Murine Lym-2 and Human-Mouse Chimeric CLL-1 Monoclonal Antibodies Against Various Human Lumphoma Cell Lines In Vitro and In Vivo." Blood vol. 90, No. 8, pp. 3150-3166 (1997).
Ginaldi et al., "Levels of expression of CD52 in normal and leukemic B and T cells: correlation with in vivo therapeutic responses to Campath-1H," Leukemia Res. 22(2):185-191 (1998).
Giusti et al., "Somatic diversification of S107 from an antiphosphocholine to an anti-DNA autoantibody is due to a single base change in its heavy chain variable region," Proc. Natl. Acad. Sci. USA 84:2926-2930 (1987).
Gorczynski and Marsden, "Modulation of CD200 receptors as a novel method of immunosuppression," Expert Opin. Ther. Patents, 13(5): 711-715(2003). See also WIPO Patent No. WO02095030 assigned to Transplantation Tech, Inc.
Gorczynski et al., "Does Successful Allopregnancy Mimic Transplantation Tolerance?", Graft, 4:338-345(2001).
Gorczynski et al., "Evidence of a role for CD200 in regulation of immune rejection of leukaemic tumour cells in C57BL/6 mice," Clin. Exp. Immunol., 126:220-229(2001).
Gorczynski et al., "Increased Expression of the Novel Molecule OX-2 IS Involved in Prolongation of Murine Renal Allograft Survival," Transplantation, vol. 65(8); pp. 1106-1114 (1998).
Gorczynski, L., et al., "Evidence That an OX-2-Positive Cell Can Inhibit the Stimulation of Type 1 Cytokine Production by Bone Marrow-Derived B7-1 (and B7-2)-Positive Dendtritic Cells," J. Immunol., 162:774-781 (1999).
Gorczynski, R., et al., "CD200 Is a Ligand for All Members of the CD200R Family of Immunoregulatory Molecules," J. Immunol., 172:7744-7749 (2004).
Gorczynski, R., et al., "Dendritic Cells Expressing TGFBeta/IL-10, and CHO Cells With OX-2, Increase Graft Survival," Transplantation Proceedings, 33:1565-1566 (2001).
Gorczynski, R.M., "Role of Cytokines in Allograft Rejection," Current Pharmaceutical Design, 7:1039-1057 (2001).
Gorczynski, R.M., "Synergy in Induction of Increased Renal Allograft Survival after Portal Vein Infusion of Dendtritic Cells Transduced to Express TGFB and IL-10, along with Administration of CHO Cells Expressing the Regulatory Molecule OX-2," Clinical Immunology, 95(3):182-189 (2000).
Gorczynski, R.M., "Transplant tolerance modifying antibody to CD200 receptor, but not CD200, alters cytokine production profile from stimulated macrophages," Eur. J. Immunol., 31:2331-2337 (2001).
Gorczynski, R.M., et al., "A CD200FC Immunoadhesin Prolongs Rat Islet Xenograft Survival in Mice," Transplantation, 73(12):1948-1953 (2002).
Gorczynski, R.M., et al., "An Immunoadhesin Incorporating the Molecule OX-2 Is a Potent Immunosuppressant That Prolongs Allo- and Xenograft Survival," J. Immunol., 163:1654-1660(1999).
Gorczynski, R.M., et al., "Anti-Rat OX-2 Blocks Increased Small Intestinal Transplant Survival After Portal Vein Immunization," Transplantation Proceedings, 31:577-578 (1999).
Gorczynski, R.M., et al., "Augmented Induction of CD4+ CD25+ Treg using Monoclonal Antibodies to CD200R," Transplantation, 79(4):488-491 (2005).
Gorczynski, R.M., et al., "Augmented Induction of CD4+ CD25+ Treg using Monoclonal Antibodies to CD200R," Transplantation, 79(9):1180-1183 (2005).
Gorczynski, R.M., et al., "CD200 Immunoadhesin Supresses Collagen-Induced Arthritis in Mice," Clinical Immunology, 101(3):328-334 (2001).
Gorczynski, R.M., et al., "Evidence for Persistent Expression of OX2 as a Necessary Component of Prolonged Renal Allograft Survival Following Portal Vein Immunization," Clinical Immunol., 97(1):69-78 (2000).

(56) References Cited

OTHER PUBLICATIONS

Gorczynski, R.M., et al., "Induction of Tolerance-Inducing Antigen-Presenting Cells in Bone Marrow Cultures In Vitor Using Monoclonal Antibodies to CD200R," Transplantation, 77(8):1 138-1144 (2004).
Gorczynski, R.M., et al., "Interleukin-13, in Combination with Anti-Interleukin-12, Increases Graft Prolongation After Portal Venous Immunization with Cultured Allogeneic Bone Marrow-Derived Dentritic Cells," Transplantation, 62(11):1592-1600 (1996).
Gorczynski, R.M., et al., "Persistent expression of OX-2 is necessary for renal allograft survival," FASEB Journal, 14(6):A1069 (2000).
Gorczynski, R.M., et al., "Receptor Engagement on Cells Expressing a Ligand for the Tolerance-Inducing Molecule OX2 Induces an Immunoregulatory Population That Inhibits Alloreactivity In Vitro and In Vivo," J. Immunol., 165:4854-4860 (2000).
Gorczynski, R.M., et al., "Regulation of Gene Expression of Murine MD-1 Regulates Subsequent T Cell Activation and Cytokine Production," J. of Immunology, 165:1925-1932 (2000).
Gorczynski, R.M., et al., "Structural and Functional Heterogeneity in the CD200R Family of Immunoregulatory Molecules and their Expression at the Fetomaternal Interface," AJRI, 52:147-163 (2004).
Gorczynski, R.M., et al., "The Same Immunoregulatory Molecules Contribute to Successful Pregnancy and Transplantation," AJRI, 48:18-26 (2002).
Gorczynski,"Evidence for an Immunoregulartory Role of OX2 with its Counter Ligand (OX2L) in the Regulation of Transplant Rejection, Fetal Loss, Autoimmunity and Tumor Growth," Archibum Immunologiae et Therapiae Experimentalis, vol. 49(4) pp. 303-309 (2001).
Gura, T., "Systems for Identifying New Drugs Are Often Faulty," Science, 278:1041-1042 (1997).
Gussow and Seemann, "Humanization of Monoclonal Antibodies," Meth. Enzymol. 203:99-121 (1991).
Hardy et al., "A lymphocyte-activating monoclonal antibody induces regression of human tumors in severe combined immunodeficient mice," Proc. Natl. Acad. Sci. USA 94:5756-5760 (1997).
Hart, P.H., "Modulation of Monocyte Effector Functions by Lipopolysacc-haride and Interferon-Y," Dept. of Medicine, University of Melbourne, Royal Melbourne Hospital, Parkville, Vic., 3050 (Abstract).
Heaney et al., "Severe asthma treatment: need for characterising patients," Lancet, 365:974-976(2005).
Hoek, R.M., et al., "Macrophage regulation by the B7.1/2 homologue OX2?", FASB Journal, 14(6):A1232 (2000).
Huang, "Structural chemistry and therapeutic intervention of protein-protein interactions in immune response, human immunodeficiency virus entry, and apoptosis," Pharmacol. Therapeutics, 86:201-215(2000).
Hutchings, N.J., et al., "Interactions of Cytoplasmic Region of OX2R Are Consistent with an Inhibitory Function," Annual Congress of the British Society for Immunology, Dec. 5-8, 2000, Harrogate, UK.
Iwanuma et al., "Antitumor Immune Response of Human Peripheral Blood Lymphocytes Coengrafted with Tumor into Severe Combined Immunodeficient Mice," Cancer Res. 57:2937-2942 (1997).
Jain, "The next frontier of molecular medicine: Delivery of therapeutics," Nature Medicine, 4(6):655-657(1998).
Jansky, L., et al., "Dynamics of Cytokine Production in Human Peripheral Blood Mononuclear Cells Stimulated by LPS or Infected by *Borrelia*," Physiol. Res., 52:593-598 (2003).
Jeurissen, S.H.M., et al., "Characteristics and functional aspects of nonlymphoid cells in rat germinal centers, recognized by two monoclonal antibodies ED5 and ED6," Eur. J. Immunol., 16:562-568 (1986).
Keil et al., "The Tolerance-Promoting Molecule OX-2 is Expressed in Fetal Trophoblast Cells that Cocoon the 'Fetal Allograft' and May Prevent Pregnancy Loss Caused by Cytokine-Activation of FGL2 Prothrombinase," Amer. J. Reprod. Immunol., 45:343(2001) (abstract).
Kim et al., "Divergent Effects of 4-1BB Antibodies on Antitumor Immunity and on Tumor-reactive T-Cell Generation," Cancer Res., 61:2031-2037(2001).
Kjaergaard et al., "Therapeutic Efficacy of OX-40 Receptor antibody Depends on Tumor Immunogenicity and Anatomic Site of Tumor Growth," Cancer Res. 60:5514-5521(2000).
Kneitz, C., et al., "Inhibition of Tcell/B cell interaction by B-CLL cells," Leukemia, 13:98-104 (1999).
Kretz-Rommel Anke et al: "CD200 Expression On Tumor Cells Suppresses Anti-Tumor Immunity: New Approaches to Cancer Immunotherapy" Journal of Immunotherapy; vol. 29, No. 6, Nov. 2006, p. 666, xp009088616 & 21st Annual Scientific Meeting Of The International-Society-For-Biological-Therapy-Of-Cancer; Los Angeles, CA, USA; Oct. 26-29, 2006 ISSN: 1524-9557.
Kretz-Rommel, "CD200 Expression on Tumor Cells Suppresses Antitumor Immunity: New Approaches to Cancer Immunotherapy," J. Immunol. 178:5595-5605 (2007).
Kretz-Rommel, A., et al., "Immune Evasion by CD200: New Approaches to Targeted Therapies for Chronic Lymphocytic Leukemia," J. Immunother., 28(6):650 (2005).
Kretz-Rommel, A., et al., "The Immuno-Regulatory Protein CD200 Is Overexpressed in a Subset of B-Cell Chronic Lymphocytic Leukemias and Plays a Role in Down-Regulating the TH1 Immune Response," J. Immunother., 27(6):S46 (2004).
Kroese, F.G.M., et al., "Germinal centre formation and follicular antigen trapping in the spleen of lethally X-irradiated and reconstituted rats," Immunology, 57:99-104 (1986).
Kroese, F.G.M., et al., "The ontogeny of germinal centre forming capacity of neonatal rat spleen," Immunology, 60:597-602 (1987).
Liu et al., "Effect of combined T- and B-cell depletion of allogenic HLA-mismatched bone marrow graft on the magnitude and kinetics of Epstein-Barr virus load in the peripheral blood of bone marrow transplant recipients," Clin. Transplant. 18:518-524 (2004).
Mariuzza et al., "The Structural Basis of Antigen-Antibody Recognition," Ann. Rev. Biophys. Biophys. Chem. 16:139-159 (1987).
Marsh, M.N., "Functional and Structural Aspects of the Epithelial Lymphocyte, with Implications for Coeliac Disease and Tropical Sprue," Univ. Dept. of Medicine, University of Manchester School of Medicine at Hope Hospital, Salford, Manchester UK pp. 55-75 (1985).
Matutes et al. Morphological and Immuniphenotypic Features of Chronic Lymphocytic Leukemia. Rev. Clin. Exp. Hematol. vol. 4.1, Mar. 2000 p. 22-47.
McCaughan et al., "Characterization of the Human Homolog of the Rat MRC OX-2 Membrane Glycoprotein," Immunogenetics, 25:329-335(1987).
McCaughan, G.M., et al., "Identification of the human homologue of the rat lymphoid/brain antigen MRC OX-2," Australian and New Zealand Journal of Medicine 17: 142 (Abstract) (1987).
McCaughan, G.W., et al., "The Gene for MRC OX-2 Membrane Glycoprotein Is Localized on Human Chromosome 3," Immunogenetics, 25:133-135 (1987).
McMaster, W.R., et al., "Identification of Ia glycoproteins in rat thymus and purification from rat spleen," Eur. J. Immunol., 9:426-433 (1979).
McWhirter, J.R., et al., "Antibodies selected from combinatorial libraries block a tumor antigen that plays a key role in immunomodulation," PNAS, 103(4):1041-1046 (2006).
Mjaaland et al., "Modulation of immune responses with monoclonal antibodies. I. Effects on regional lymph node morphology and on anti-hapten responses to haptenized monoclonal antibodies", Eur. J. Immunol., 20:1457-1461(1990).
Mjaaland, S., et al., "The Localization of Antigen in Lymph Node Follicles of Congenitally Athymic Nude Rats," Scand. J. Immunol., 26:141-147 (1987).
Mohammad, R.M., et al., "Establishment of a human B-CLL xenograft model: utility as a preclinical therapeutic model," Leukemia, 10:130-137 (1996).
Mori et al., "Establishment of a new anit-cancer drugs-resistant cell line derived from B-chronic lymphocyctic leukemia" Proceedings, Fifty-Ninth Annual Meeting of teh Japanese Cancer Association, p. 583, # 3788 (Sep. 1, 2000).

(56) References Cited

OTHER PUBLICATIONS

Morris, R.J., et al., "Sequential Expression of OX2 and Thy-1 Glycoproteins on the Neuronal Surface during Development," Dev. Neurosci., 9:33-44 (1987).
Myers et al., "Characterization of a Peptide Analog of a Determinant of Type II Collagen that Suppresses Collagen-Induced Arthritis," J. of Immunology, 3589-3595(1998).
Nagelkerken L., et al., "Accessory Cell Function of Thoracic Duct Nonlymphoid Cells, Dentritic Cells, and Splenic Adherent Cells in the Brown-Norway Rat," Cellular Immunology, 93:520-531 (1985).
Nathan and Muller, "Putting the Brakes on innate immunity: a regulatory role for CD200?", Nat Immunol., 2(1):17-19(2001).
Ni et al., "An immunoadhesin incorporating the molecule OX-2 is a potent immunosuppressant which prolongs allograft survival", FASEB Journal 13(5):A983(1999).
Pardoll, Drew., "Therapeutic Vaccination for Cancer," Clin. Immunol., 95(1):544-562(2000).
Paterson, D.J., et al., "Antigens of Activated Rat T Lymphocytes Including A Molecule of 50,000 Mr Detected Only on CD4 Positive T Blasts," Molecular Immunology, 24(12):1281-1290 (1987).
Preston et al., "The leukocyte/neuron cell surface antigen OX2 binds to a ligand on macrophages", European J. of Immunol., 27(8):1911-1918(1997).
Ragheb et al., "Preparation and functional properties of monoclonal antibodies to human, mouse and rat OX-2", Immunol. Letters, 68(2,3):311-315(1999).
Ragheb, R.F., "Exploration of OX-2 function in tolerance induction and graft acceptance using an anti-mouse OX-2 monoclonal antibody," Masters Abstracts International, 38(4):971-972 (2000).
Richards, S.J., et al., "Reported Sequence Homology Between Alzheimer Amyloid770 and the MCR OX-2 Antigen Does Not Predict Function," Brain Research Bulletin, 38(3):305-306 (1995).
Riley, "Melanoma and the Problem of Malignancy," J. Exp. Med. 204:1-9 (2004).
Rioux, P., Campath-1H (Cambridge Univeristy), IDrugs, vol. 2(2); pp. 153-167, Database Medline, abstract No. NLM16160950 (Abstract Only) (1999).
Romagnani, Sergio., "Short Analytical Review: TH1 and TH2 in Human Diseases," Clin. Immunol. Immunopath, 80(3):225-235(1996).
Rosenblum, M.D., et al., "CD200 is a novel p53-target gene involved in apoptosis-associated immune tolerance," Blood, 103(7):2691-2698 (2004).
Rosenwald et al., "Relation of Gene Expression Phenotype to Immunoglobulin Mutation Genotype in B Cell Chronic Lymphocytic Leukemia," J. of Exp. Medicine, 194(11):1639-1647(2001).
Rudicoff et al., "Single amino acid substitution altering antigen-binding specificity," Proc. Natl. Acad. Sci. USA 79:1979-1983 (1982).
Sahin et al., "New monoclonal antibody specific for a 6.5 kDa glycoprotein which presents mainly on a B cell of chronic lymphocytic leukemia (CLL)" Immunology Letters, 2001, 76, 1-6.
Schlom, Jeffrey :Monoclonal Antiboides They're More and Less Than You Think, Molecular and Cellular Research for Future Diagnosis and Therapy, 95-134, 1991.
Schultes et al., "Immunotherapy of Human Ovarian Carcinoma with OVAREX™ MAb-B43.13 in a Human-PBL-SCID/BG Mouse Model," Hybridoma 18(1):47-55 (1999).
Sebestyen et al., Syndecan-1 (CD138) expression in human non-Hodgkin lymphomas. British Jounal of Hematology. vol. 104, 1999, p. 412-419.
Sehgal, et al., "Generation of the Primary Antibody Repertoire in Rabbits: Expression of a Diverse Set of Igk-V Genes May Compensate for Limited Combinatorial Diversity at the Heavy Chain Locus," Immunogenetics 50:31-42 (1999).
Snyder et al., "Enhanced Targeting and Killing of Tumor Cells Expressing the CXC Chemokine Receptor 4 by Transducible Anticancer Peptides," Cancer Res. 65(23):10646-10650 (2005).
Srivastava, P.K., "Immunotherapy of human cancer: lessons from mice," Nature Immunology, 1(5):363-366 (2000).

Steinman, Lawrence, "Assessment of Animal Models for MS and Demyelinating Disease in the Design of Rational Therapy," Neuron, 24:511-514(1999).
Syme, R., et al., "Comparison of CD34 and Monocyte-Derived Dendritic Cells from Mobilized Peripheral Blood from Cancer Patients," Stem Cells, 23:74-81 (2005).
Tanaka et al., "The Anti-Human Tumor Effect and Generation of Human Cytotoxic T Cells in SCID Mice Given Human Peripheral Blood Lymphocytes by the in Vivo Transfer of the Interleukin-6 Gene Using Adenovirus Vector," Cancer Res. 57:1335-1343 (1997).
Tang et al., Pathogenesis of collagen-induced arthritis: modulation of disease by arthritogenic T-Cell epitope location, J. of Immunology, 113: 384-391.
Tangri and Raghupathy, "Expression of Cytokines in Placentas of Mice Undergoing Immunologically Mediated Spontaneous Fetal Resorptions," Biology of Reprod., 49:850-856(1993).
Taylor, N., et al., "Enhanced Tolerance to Autoimmune Uveitis in CD200-Deficient Mice Correlates with a Pronounced Th2 Switch in Response to Antigen Challenge," J. Immunol., 174:143-154 (2005).
Thomsen et al., "Reconstitution of a human immune system in immunodeficient mice: models of human alloreaction in vivo," Tissue Antigens 66:73-82 (2005).
Toder et al., "Mouse Model for the Treatment of Immune Pregnancy Loss," Am. J. of Reprod. Immunol., 26:42-46(1991).
Webb, M., et al., "Localisation of the MRC OX-2 Glycoprotein on the Surfaces of Neurones," J. Neurochemistry, 43:1061-1067 (1984).
Wilczynski, J.R., "Immunoligical Analogy Between Allograft Rejection, Recurrent Abortion and Pre-Eclampsia—the Same Basic Mechanism?," Human Ummunology, 67:492-511 (2006).
Wright et al., "The unusual distribution of the neuronal/lymphoid cell surface CD200 (OX2) glycoprotein is conserved in himans," Immunology 102:173-179 (2001).
Wright, G.J., et al., "Lymphoid/Neuronal Cell Surface OX2 Glycoprotein Recognizes a Novel Receptor on Macrophages Implicated in the Control of Their Function," Immunity, 13:233-242 (2000).
Wright, G.J., et al., "The lymphoid/neuronal OX-2 glycoprotein interacts with a novel protein expressed by macrophages," Tissue Antigens, 55 (Supplement 1); vol. 1 (2000).
Wright, G.J., et al., "Viral homologues of cell surface proteins OX2 and CD47 have potential to regulate macrophage function," Annual Congress of the British Society for Immunology, vol. 101 (Supplement 1): 50 Dec. 5-8, 2000.
Yang, C., et al., "Functional maturation and recent thymic emigrants in teh periphery: development of alloreactivity correlates with the cyclic expression of CD45RC isoforms," Eur. J. Immunol., 22:2261-2269 (1992).
Yu, X., et al., "The role of B7-CD28 co-stimulation in tumor rejection," International Immunology, 10(6):791-797 (1998).
Zhang, S., et al., "Molecular Mechanisms of CD200 Inhibition of Mast Cell Activation," J. Immunol., 173:6786-6793 (2004).
Zheng, P., et al., "B7-CTLA4 interaction enhances both production of antitumor cytotoxic T lymphocytes and resistance to tumor challenge," Proc. Natl. Acad. Sci. USA, 95:6284-6289 (1998).
Zhu et al., "Radioimmunotherapy of Human B-Cell Chronic Lymphocytic Leukemia in Nude Mice." Cancer Research. 54, 5111-5117 (1994).
Zips, D., et al., "New Anticancer Agents: In Vitro and In Vivo Evaluation," in vivo, 19:1-7 (2005).
Zou et al. Human Glioma-Induced Immunosuppression Involves Soluble Factor(s) That Alters Monocyte Cytokine Profile and Surface Markers. vol. 162, pp. 4882-4892 (1999).
Bruggemann et al., "A Matched Set of Rat/Mouse Chimeric Antibodies: Identification and Biological Properties of Rat H Chain Constant Regions μ, γ1, γ2a, γ2b, γ2c, ε, and α1," The Journal of Immunology, vol. 142(9), pp. 3145-3150 (1989).
Smith-Gill, Sandra J., "Biology of Antibody-Mediated Responses," Biologic Therapy of Cancer: Principles and Practice, Chapter 2, pp. 39-51 (1995).

(56) References Cited

OTHER PUBLICATIONS

Mueller et al., "Aglycosylated chimeric mouse/human IgG1 antibody retains some effector function," Hybridoma, vol. 10(2), pp. 211-217 (1991) (abstract).

Mueller et al., "Humanized Porcine VCAM-Specific Monoclonal Antibodies With Chimeric IgG2/G4 Constant Regions Block Human Leukocyte Binding to Porcine Endothelial Cells," Molecular Immunology, vol. 34(6), pp. 441-452 (1997).

Yamaguchi et al., "Application of monoclonal antibody for drug delivery system—Missile therapy for cancer," Nihon Rinsho, vol. 56(3), pp. 638-643 (1998).

Yamaguchi et al., "Application of tumor marker for immunotargeting therapy of cancer," Nihon Rinsho, vol. 54(6), pp. 1674-1679 (1996).

Yamaguchi et al., "Biological Response Modifier and Missile Cancer Chemotherapy," Biotherapy, vol. 10(4), pp. 605-609 (1996).

McWhirter et al., Supplemental Materials, PNAS, vol. 103, pp. 1041-1046 (2006).

Presta, L., "Antibody engineering for therapeutics," Current Opinion in Structural Biology, 13(4):519-525 (2003).

Dorai et al., "Aglycosylated Chimeric Mouse/Human IgG1 Antibody Retains Some Effector Function," Hybridoma, vol. 10(2): 211-217 (1991).

* cited by examiner

METHODS AND COMPOSITIONS FOR TREATING AUTOIMMUNE DISEASE

RELATED APPLICATIONS

This application is a national stage filing under 35 U.S.C. 371 of International Application PCT/US2008/009030, filed Jul. 25, 2008, which claims the benefit of U.S. Provisional Patent Application Ser. No. 60/962,044, filed Jul. 25, 2007, the disclosures of which are incorporated herein by reference in their entirety. International Application PCT/US2008/009030 was published under PCT Article 21(2) in English.

TECHNICAL FIELD

The disclosure relates to OX-2/CD200 (herein referred to as CD200) antibodies and methods of treating autoimmune disease.

BACKGROUND

Autoimmunity is the failure of an organism to recognize its own constituent parts (down to the sub-molecular levels) as "self", which results in an immune response against its own cells and tissues. Any disease that results from such an aberrant immune response is termed an autoimmune disease. In order to inhibit harmful immune reactions in such instances, immunosuppressive agents such as corticosteroids and cytokine antagonists may be administered to patients. However these general immunosuppressives can elicit undesirable side effects including toxicity and reduced resistance to infection. Thus alternative, and perhaps more specific, methods of treating autoimmunity are needed.

Several immunomodulatory therapies, including antibody therapies, have proven successful in the treatment of certain autoimmune disorders. However there is a clinical need for additional antibody therapies for the treatment of autoimmune disorders. Furthermore, there is a related need for humanized or other chimeric human/mouse monoclonal antibodies. In well publicized studies, patients administered murine anti-TNF (tumor necrosis factor) monoclonal antibodies developed anti-murine antibody responses to the administered antibody (Exley A. R., et al., *Lancet* 335:1275-1277 (1990)). This type of immune response to the treatment regimen, commonly referred to as the human anti-mouse antibody (HAMA) response (Mirick et al. *Q J Nucl Med Mol Imaging* 2004; 48: 251-7), decreases the effectiveness of the treatment and may even render the treatment completely ineffective. Humanized or chimeric human/mouse monoclonal antibodies have been shown to significantly decrease the HAMA response and to increase the therapeutic effectiveness of antibody treatments. See, for example, LoBuglio et al., *Proc. Natl. Acad. Sci. USA* 86:4220-4224 (June 1989). Furthermore, antibodies in which particular functionalities are either enhanced or reduced may find useful applications in the clinic.

CD200, a molecule expressed on the surface of numerous cell types including B cells, some T cells and dendritic cells and other cells, which possesses a high degree of homology to molecules of the immunoglobulin gene family, has previously been thought to be implicated in immune suppression (Gorczynski et al., *Transplantation* 65:1106-1114 (1998)). The prior art appears to show, for example, that CD200-expressing cells can inhibit the stimulation of Th1 cytokine production.

SUMMARY

In certain aspects the disclosure provides a method for treating a patient with an autoimmune disease, said method comprising administering a therapeutically effective amount of an anti-CD200 antibody or antigen-binding fragment thereof to said patient. In certain embodiments, said autoimmune disease is selected from the group including but not limited to rheumatoid arthritis, inflammatory bowel disease, systemic lupus erythematosus, multiple sclerosis, Hashimoto's thyroiditis, pernicious anemia, Addison's disease, type I diabetes, dermatomyositis, Sjogren's syndrome, lupus erythematosus, myasthenia gravis, Reiter's syndrome, idiopathic thrombocytopenic purpura, hemolytic anemia, Wegener's granulomatosis, refractory dermatomyositis, cold agglutinin disease associated with indolent lymphoma, acquired factor VIII inhibitors disease and Grave's disease.

In certain embodiments, said antibody or antigen-binding fragment thereof blocks the production of auto-antibodies. In certain embodiments, said auto-antibodies are selected from IgG1, IgG2, IgG3, IgG4, IgM, IgA1, IgA2, IgA, IgD, and/or IgE immunoglobulins. In certain embodiments, said antibody or antigen-binding fragment thereof does not block the production of auto-antibodies.

In certain embodiments, said antibody or antigen-binding fragment thereof is an antagonistic antibody. In certain embodiments, said antibody or antigen-binding fragment thereof is an agonistic antibody.

In certain embodiments, said antibody or antigen-binding fragment thereof modulates expression of cytokines in said patient. In certain embodiments, said antibody or antigen-binding fragment thereof enhances production of a cytokine in said patient selected from the group consisting of: IL-12, IL-10 and IL-4.

In certain embodiments, said antibody or antibody fragment thereof is selected from the group consisting of a polyclonal antibody, a monoclonal antibody or antibody fragment thereof, a recombinant antibody, a diabody, a chimerized or chimeric antibody or antibody fragment thereof, a humanized antibody or antibody fragment thereof, a deimmunized human antibody or antibody fragment thereof, a fully human antibody or antibody fragment thereof, a single chain antibody, an Fv, an Fd, an Fab, an Fab', and an F(ab')$_2$. In certain embodiments, said antibody is a monoclonal antibody. In certain embodiments, said anti-CD200 antibody or antibody fragment thereof is conjugated to a molecule selected from the group consisting of a polymer and a polypeptide. In certain embodiments, said polymer is poly(ethylene) glycol.

In certain embodiments, said antibody or antigen-binding fragment thereof is administered for at least one month to said mammal. In certain embodiments, said antibody or antigen-binding fragment thereof is administered for at least one year to said mammal. In certain embodiments, said antibody or antigen-binding fragment thereof is administered chronically to said mammal.

In certain embodiments, said antibody or antigen-binding fragment thereof is administered systemically to said mammal. In certain embodiments, said antibody or antigen-binding fragment thereof is administered locally to said mammal.

In certain embodiments, the methods of the disclosure further comprise administering a second agent or therapy. In certain embodiments, the second agent comprises one or more of the following characteristics: a) regulatory activity on T cells; and b) immunomodulatory activity. In certain embodiments, said second agent or therapy is selected from the group consisting of an immunosuppressive agent, immunomodulatory agent, heteroclitic peptide, antibody, antigen-binding fragment, nucleic acid, small molecule, organometallic compound, polypeptide, aptamer, spiegelmer, chemical, inorganic compound, metal, prodrug, and peptidomimetic compound. In certain embodiments, the immunomodulatory or immunosuppressive agent is a calcineurin inhibitor. In certain embodiments, the calcineurin inhibitor is selected from tacrolimus (FK-506) and cyclosporine A. In certain embodiments, the immunomodulatory or immunosuppressive agent is selected from the group consisting of adriamycin, azathiopurine, busulfan, cyclophosphamide, cyclosporine A, Cytoxan, fludarabine, 5-fluorouracil, methotrexate, mycophenolate mofetil, a nonsteroidal anti-inflammatory, sirolimus (rapamycin), and tacrolimus (FK-506). In certain embodiments, the immunomodulatory or immunosuppressive agent is an antibody selected from the group consisting of muromonab-CD3, alemtuzumab, basiliximab, daclizumab, rituximab, IVIg and anti-thymocyte globulin. In certain embodiments, said second agent is administered either sequentially or simultaneously.

The invention contemplates combinations of any of the foregoing aspects and embodiments of the invention. Other embodiments are described in the description. All references cited herein are hereby incorporated by reference.

DETAILED DESCRIPTION OF PREFERRED EMBODIMENTS

I. Overview

Figure 1:
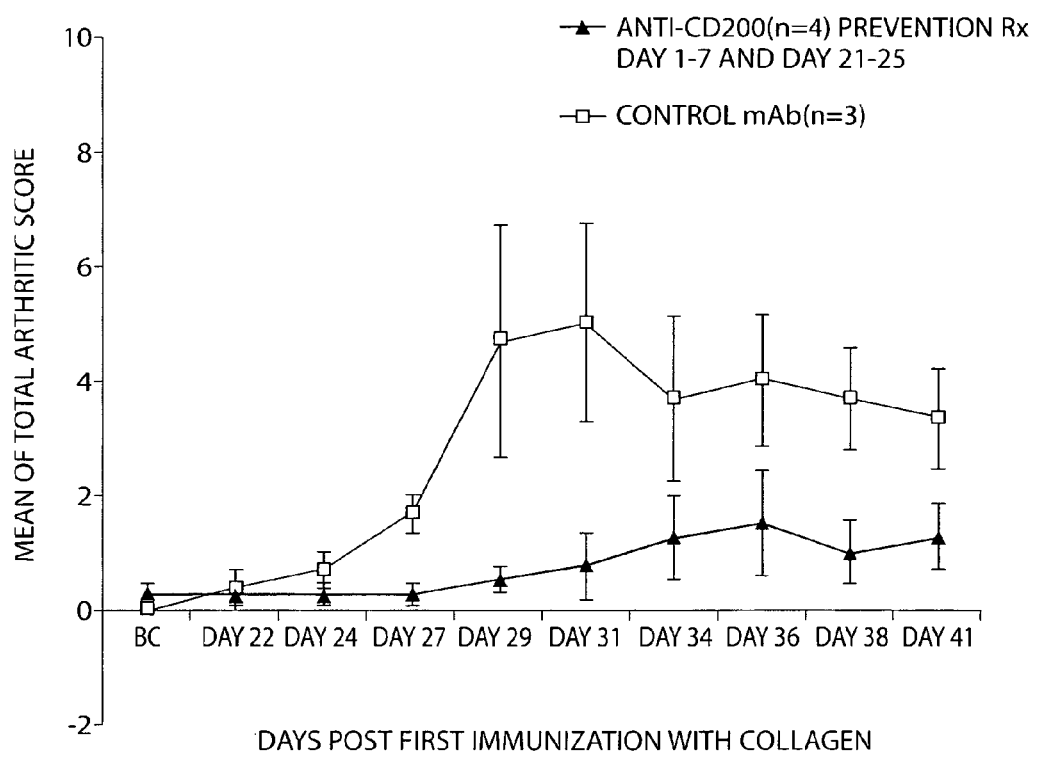
FIG. 1 shows anti-CD200 treatment reduces the severity of collagen induced arthritis. DBA/1LacJ mice were administered 5 mg/kg dose of either anti-CD200 or isotype-matched control mAb by i.p. injection from day 1 to day 7 and day 21 to day 25 after initial BCII immunization on day 1. Data are presented as mean±SEM.

Prior art, especially numerous articles by Gorczynski, has seemed to indicate that the molecule CD200 is immunosuppressive. For example, Gorczynski et al., Clin. Immunol. 104:256-264 (2002) teaches that in a collagen-induced arthritis (CIA) model in mice treatment with CD200 (in a CD200Fc form) ameliorates CIA. They state that work has shown that CD200 binds its receptor and the immunosuppressive activity is via the receptor. The paper teaches that use of an anti-CD200 receptor antibody that crosslinks the receptor has this same activity of ameliorating CIA, the antibody apparently being an agonistic antibody. It is likely that CD200, which is a member of the Ig superfamily, acts similarly to an antibody and acts to crosslink the CD200 receptor thereby activating the receptor which in turn results in immunosuppression.

Based on the prior art, one would expect that treatment of an animal or patient with an anti-CD200 antibody should result in an enhanced immune response. The logic is that antibodies to CD200 would bind the CD200 thereby preventing CD200 from binding to its receptor. Without a CD200: CD200 receptor interaction the CD200 receptor would not be activated and there would be no immune suppression, thereby resulting in enhanced inflammation or autoimmune effect. For diseases such as CIA this would mean that treatment with anti-CD200 should exacerbate the disease.

II. CD200 Antibodies

CD200 is a highly conserved type I transmembrane glycoprotein expressed on various cell types including cells of the immune system (e.g., T-cells, B-cells, and dendritic cells (Barclay et al., 2002 *TRENDS Immunol.* 23:285-290)). The protein interacts with its receptor CD200R on myeloid cells and sub-populations of T cells (Wright et al. *J. Immunol.* 2003 171: 3034-3046 and Wright et al., *Immunity* 2000 13:233-242); the CD200:CD200R interaction has been thought to deliver an immunomodulatory signal to cells and induce immunosuppression including apoptosis-associated immune tolerance (Rosenblum et al. 2004 *Blood* 103: 2691-2698). Thus it has been thought that agents that modulate the function or activity of CD200 and/or its receptor may result in enhanced immunosuppressive effects. In addition, agents that specifically bind CD200 (but that may or may not modulate the CD200:CD200R interaction) may trigger downstream events that modulate the effects of CD200.

In certain aspects, the present disclosure relates to CD200 modifiers. As used herein, the term modifier includes any agent that is capable of modulating the activity, function and/or the expression of CD200 or its receptor. Examples include but are not limited to polypeptides, antibodies, small molecules, aptamers, spiegelmers, locked nucleic acid (LNA) inhibitors, peptide nucleic acid (PNA) inhibitors, nucleic acid constructs (e.g., gene-targeting constructs, antisense constructs, RNA interference (RNAi) constructs, etc.) and peptidomimetics. In certain embodiments, the antibody disrupts the interaction of CD200 and CD200R. In other embodiments, the CD200 antibodies are capable of increasing the immunosuppressive effects of CD200 or are capable of targeting CD200-expressing cells for depletion or elimination.

In certain aspects, the CD200 modifiers are polypeptides. Polypeptides utilized in the present disclosure can be constructed using different techniques which are known to those skilled in the art. In one embodiment, the polypeptides are obtained by chemical synthesis. In other embodiments, the polypeptides are constructed from a fragment or several fragments. In further embodiments, the polypeptide is an anti-CD200 antibody as described herein.

As used herein, the term "antibodies" refers to complete antibodies or antibody fragments capable of binding to CD200 or CD200R. Included are Fab, Fv, scFv, Fab' and F(ab')$_2$, monoclonal and polyclonal antibodies, engineered antibodies (including chimeric, single chain, CDR-grafted, humanized, fully human antibodies, and artificially selected antibodies), and synthetic or semi-synthetic antibodies produced using phage display or alternative techniques. Also included are antibodies engineered or produced in ways to contain variant or altered constant or Fc regions with either increased or decreased ability to bind one or more effector cells; such variant antibodies include but are not limited to antibodies in which the constant or Fc region contains altered glycosylation patterns. Small fragments, such as Fv and scFv, possess advantageous properties for diagnostic and therapeutic applications on account of their small size and consequent superior tissue distribution. Antibodies with engineered or variant constant or Fc regions can be useful in modulating effector functions, such as, for example, ADCC and CDC. Such antibodies with engineered or variant constant or Fc regions may be useful in instances where CD200 is expressed in normal tissue, for example; variant anti-CD200 antibodies without effector function in these instances may elicit the desired therapeutic response while not damaging normal tissue. Furthermore, antibodies, variant antibodies, and fragments thereof may be blocking (i.e., the antibodies or fragments inhibit the interaction of CD200 and CD200R) or agonistic (i.e., the antibodies or fragments enhance the interaction of CD200 and CD200R).

The disclosure also relates to anti-CD200 antibodies comprising heavy and light chains as provided herein, including heavy and light chains that are homologous or similar to the heavy and/or light chains provided herein. "Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. The term "homology" describes a mathematically based comparison of sequence similarities which is used to identify genes or proteins with similar functions or motifs. As used herein, "identity" means the percentage of identical nucleotide or amino acid residues at corresponding positions in two or more sequences when the sequences are aligned to maximize sequence matching, i.e., taking into account gaps and insertions. Thus methods to determine identity are designed to give the largest match between the sequences tested (see Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., Stockton Press, New York, 1991; and Carillo, H., and Lipman, D., SIAM J. Applied Math., 48: 1073 (1988), Devereux, J., et al., Nucleic Acids Research 12(1): 387 (1984), BLASTP, BLASTN, FASTA (Altschul, S. F. et al., J. Mol. Biol. 215: 403-410 (1990) and Altschul et al. Nucleic Acids Res. 25: 3389-3402 (1997)) and BLAST X (BLAST Manual, Altschul, S., et al., NCBI NLM NIH Bethesda, Md. 20894; Altschul, S., et al., J. Mol. Biol. 215: 403-410 (1990)). A sequence which is "unrelated" or "non-homologous" shares less than 40% identity, though preferably less than 25% identity with a sequence of the present disclosure. In comparing two sequences, the absence of residues (amino acids or nucleic acids) or presence of extra residues also decreases the identity and homology/similarity.

Accordingly, the disclosure relates to antibodies as described herein without the leader sequences. Thus antibodies of the disclosure may comprise heavy and light chains (as described herein) in which the leader sequence is either absent or replaced by a different leader sequence. If host cells are used to produce antibodies of the present disclosure, appropriate leader sequences may therefore be selected according to the particular host cell used.

Antibodies may be produced by methods well known in the art. For example, monoclonal anti-CD200 antibodies may be generated using CD200 positive cells, CD200 polypeptide, or a fragment of CD200 polypeptide, as an immunogen, thus raising an immune response in animals from which antibody-producing cells and in turn monoclonal antibodies may be isolated. The sequence of such antibodies may be determined and the antibodies or variants thereof produced by recombinant techniques. Recombinant techniques may be used to produce chimeric, CDR-grafted, humanized and fully human antibodies based on the sequence of the monoclonal antibodies as well as polypeptides capable of binding to CD200.

Moreover, antibodies derived from recombinant libraries ("phage antibodies") may be selected using CD200-positive cells, or polypeptides derived therefrom, as bait to isolate the antibodies or polypeptides on the basis of target specificity. The production and isolation of non-human and chimeric anti-CD200 antibodies are well within the purview of the skilled artisan.

Recombinant DNA technology is used to improve the antibodies produced in non-human cells. Thus, chimeric antibodies may be constructed in order to decrease the immunogenicity thereof in diagnostic or therapeutic applications. Moreover, immunogenicity may be minimized by humanizing the antibodies by CDR grafting and, optionally, framework modification. See, U.S. Pat. No. 5,225,539, the contents of which are incorporated herein by reference.

Antibodies may be obtained from animal serum or, in the case of monoclonal antibodies or fragments thereof, produced in cell culture. Recombinant DNA technology may be used to produce the antibodies according to established procedure, including procedures in bacterial or preferably mammalian cell culture. The selected cell culture system preferably secretes the antibody product.

In another embodiment, a process for the production of an antibody disclosed herein includes culturing a host, e.g. *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic, for example bicistronic, DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibers, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane. After one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules are described in the above references and also in, for example WO97/08320; U.S. Pat. No. 5,427,908; U.S. Pat. No. 5,508,717; Smith, 1985, Science, Vol. 225, pp 1315-1317; Parmley and Smith, 1988, Gene 73, pp 305-318; De La Cruz et al., 1988, Journal of Biological Chemistry, 263 pp 4318-4322; U.S. Pat. No. 5,403,484; U.S. Pat. No. 5,223,409; WO88/06630; WO92/15679; U.S. Pat. No. 5,780,279; U.S. Pat. No. 5,571,698; U.S. Pat. No. 6,040,136; Davis et al., 1999, Cancer Metastasis Rev., 18(4):421-5; Taylor, et al., Nucleic Acids Research 20 (1992): 6287-6295; Tomizuka et al., Proc. Natl. Academy of Sciences USA 97(2) (2000): 722-727. The contents of all these references are incorporated herein by reference.

The cell culture supernatants are screened for the desired antibodies, preferentially by immunofluorescent staining of CD200-positive cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with one or more surface polypeptides derived from a CD200-positive cell line, or with Protein-A or -G.

Another embodiment provides a process for the preparation of a bacterial cell line secreting antibodies directed against CD200 in a suitable mammal. For example a rabbit is immunized with pooled samples from CD200-positive tissue or cells or CD200 polypeptide or fragments thereof. A phage display library produced from the immunized rabbit is constructed and panned for the desired antibodies in accordance with methods well known in the art (such as, for example, the methods disclosed in the various references incorporated herein by reference).

Hybridoma cells secreting the monoclonal antibodies are also disclosed. The preferred hybridoma cells are genetically stable, secrete monoclonal antibodies described herein of the desired specificity, and can be expanded from deep-frozen cultures by thawing and propagation in vitro or as ascites in vivo.

In another embodiment, a process is provided for the preparation of a hybridoma cell line secreting monoclonal antibodies against CD200. In that process, a suitable mammal, for example a Balb/c mouse, is immunized with one or more polypeptides or antigenic fragments of CD200 or with one or more polypeptides or antigenic fragments derived from a CD200-positive cell, the CD200-positive cell itself, or an antigenic carrier containing a purified polypeptide as described. Antibody-producing cells of the immunized mammal are grown briefly in culture or fused with cells of a suitable myeloma cell line. The hybrid cells obtained in the fusion are cloned, and cell clones secreting the desired antibodies are selected. For example, spleen cells of Balb/c mice immunized with a CD200-positive Chronic Lymphocytic Leukemia (CLL) cell line are fused with cells of the myeloma cell line PAI or the myeloma cell line Sp2/0-Ag 14. The obtained hybrid cells are then screened for secretion of the desired antibodies and positive hybridoma cells are cloned.

Preferred is a process for the preparation of a hybridoma cell line, characterized in that Balb/c mice are immunized by injecting subcutaneously and/or intraperitoneally between $10^6$ and $10^7$ cells of a CD200-positive cell line several times, e.g. four to six times, over several months, e.g. between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described hereinbefore, supplemented with a selection medium, for example HAT medium, at regular intervals in order to prevent normal myeloma cells from overgrowing the desired hybridoma cells.

The antibodies and fragments thereof can be "chimeric". Chimeric antibodies and antigen-binding fragments thereof comprise portions from two or more different species (e.g., mouse and human). Chimeric antibodies can be produced with mouse variable regions of desired specificity spliced into human constant domain gene segments (for example, U.S. Pat. No. 4,816,567). In this manner, non-human antibodies can be modified to make them more suitable for human clinical application.

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction.

Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art. For example, humanization can be essentially performed following the method of Winter and co-workers (Jones et al., Nature 321: 522-525 (1986); Riechmann et al., Nature, 332:323-327 (1988); Verhoeyen et al., Science, 239: 1534-1536 (1988)), by substituting rodent CDRs or CDR sequences for the corresponding sequences of a human antibody. Also see Staelens et al. 2006 Mol Immunol 43: 1243-1257. In particular embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production (see, e.g., Jakobovits et al., Proc. Natl. Acad. Sci. USA, 90:2551 (1993); Jakobovits et al., Nature, 362:255-258 (1993); Bruggemann et al., Year in Immunol., 7:33 (1993); and Duchosal et al. Nature 355:258 (1992). Transgenic mice strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein (e.g., CD200, fragments thereof, or cells expressing CD200) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

In addition, human antibodies can be derived from phage-display libraries (Hoogenboom et al., J. Mol. Biol., 227:381 (1991); Marks et al., J. Mol. Biol., 222:581-597 (1991); Vaughan et al. Nature Biotech 14:309 (1996)). Synthetic phage libraries can be created which use randomized combinations of synthetic human antibody V-regions. By selection on antigen fully human antibodies can be made in which the V-regions are very human-like in nature. See U.S. Pat. Nos. 6,794,132, 6,680,209, 4,634,666, and Ostberg et al. (1983), Hybridoma 2:361-367, the contents of which are incorporated by reference.

For the generation of human antibodies, also see Mendez et al. Nature Genetics 15:146-156 (1997), Green and Jakobovits J. Exp. Med. 188:483-495 (1998), the disclosures of which are hereby incorporated by reference. Human antibodies are further discussed and delineated in U.S. Pat. Nos. 5,939,598 and 6,673,986. Also see U.S. Pat. Nos. 6,114,598, 6,075,181, and 6,162,963, all filed Jun. 5, 1995. Also see U.S. Pat. No. 6,150,584, filed Oct. 2, 1996 and U.S. Pat. Nos. 6,713,610 and 6,657,103 as well as U.S. patent application Ser. No. 10/421,011 (US 2003-0229905 A1), Ser. No. 10/455,013 (US 2004-0010810 A1), Ser. No. 10/627,250 (US 2004-0093622 A1), Ser. No. 10/656,623 (US 2006-0040363 A1), Ser. No. 10/658,521 (US 2005-0054055 A1), Ser. No. 10/917,703 (US 2005-0076395 A1) and Ser. No. 10/978,297 (US 2005-0287630 A1). See also PCT/US93/06926 filed on Jul. 23, 1993, European Patent No. EP 0 463 151 B1, grant published Jun. 12, 1996, International Patent Application No. WO 94/02602, published Feb. 3, 1994, International Patent Application No. WO 96/34096, published Oct. 31, 1996, and WO 98/24893, published Jun. 11, 1998. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661, 016, 5,770,429, 5,789,650, and 5,814,318 each to Lonberg and Kay, U.S. Pat. No. 5,591,669 to Krimpenfort and Berns, U.S. Pat. Nos. 5,612,205, 5,721,367, 5,789,215 to Berns et al., and U.S. Pat. No. 5,643,763 to Choi and Dunn, and GenPharm International. Also see U.S. Pat. Nos. 5,569,825, 5,877,397, 6,300,129, 5,874,299, 6,255,458, and 7,041,871, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of which are hereby incorporated by reference in their entirety. See further Taylor et al. (1992 Nucleic Acids Res., 20: 6287), Chen et al. (1993 Int. Immunol. 5: 647), Tuaillon et al. (1993 Proc. Natl. Acad. Sci. USA, 90: 3720-4), Choi et al., (1993 Nature Genetics 4: 117), Lonberg et al. (1994 Nature 368: 856-859), Taylor et al. (1994 International Immunology 6: 579-591), and Tuaillon et al. (1995 J. Immunol. 154: 6453-65), Fishwild et al. (1996 Nature Biotechnology 14: 845), and Tuaillon et al. (2000 Eur. J. Immunol. 10: 2998-3005), the disclosures of which are hereby incorporated by reference in their entirety.

In certain embodiments, de-immunized anti-CD200 antibodies or antigen-binding fragments thereof are provided. De-immunized antibodies or antigen-binding fragments thereof may be modified so as to render the antibody or antigen-binding fragment thereof non-immunogenic, or less immunogenic, to a given species. De-immunization can be achieved by modifying the antibody or antigen-binding fragment thereof utilizing any of a variety of techniques known to those skilled in the art (see e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized anti-CD200 antibodies described herein include de-immunized antigen-binding fragments, Fab, Fv, scFv, Fab' and F(ab')$_2$, monoclonal antibodies, murine antibodies, engineered antibodies (such as, for example, chimeric, single chain, CDR-grafted, humanized, fully human antibodies, and artificially selected antibodies), synthetic antibodies and semi-synthetic antibodies.

In a further embodiment, recombinant DNA comprising an insert coding for a heavy chain variable domain and/or for a light chain variable domain of antibodies directed to CD200 or a CD200-positive cell line are produced. The term DNA includes coding single stranded DNAs, double stranded DNAs consisting of said coding DNAs and of complementary DNAs thereto, or these complementary (single stranded) DNAs themselves.

Furthermore, DNA encoding a heavy chain variable domain and/or a light chain variable domain of antibodies directed to CD200 or the CD200-positive cell line can be enzymatically or chemically synthesized DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted, inserted, or exchanged with one or more other amino acids. Preferably said modification(s) are outside the CDRs of the heavy chain variable domain and/or of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an antibody directed to CD200 or a CD200-positive cell line fused to a human constant domain IgG, for example γ1, γ2, γ3 or γ4, in particular embodiments γ1 or γ4, may be used. Recombinant DNAs including an insert coding for a light chain murine variable domain of an antibody fused to a human constant domain κ or λ, preferably κ, are also provided.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent. The DNA coding for an agent is intended to be a DNA coding for the agent useful in diagnostic or therapeutic applications. Thus, agent molecules which are toxins or enzymes, especially enzymes capable of catalyzing the activation of prodrugs, are particularly indicated. The DNA encoding such an agent has the sequence of a naturally occurring enzyme or toxin encoding DNA, or a mutant thereof, and can be prepared by methods well known in the art.

Accordingly, the monoclonal antibodies or antigen-binding fragments of the disclosure can be naked antibodies or antigen-binding fragments that are not conjugated to other agents, for example, a therapeutic agent or detectable label. Alternatively, the monoclonal antibody or antigen-binding fragment can be conjugated to an agent such as, for example, a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an anti-CD200 polypeptide or antigen-binding fragment (e.g., Fab, Fv, single-chain scFv, Fab' and F(ab')$_2$) is linked to a molecule that increases the half-life of the polypeptide or antigen-binding fragment. Molecules that may be linked to said anti-CD200 polypeptide or antigen-binding fragment include but are not limited to serum proteins including albumin, polypeptides, other proteins or protein domains, and PEG.

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as E. coli gpt (Mulligan, R. C. and Berg, P., Proc. Natl. Acad. Sci., USA, 78: 2072 (1981)) or Tn5 neo (Southern, P. J. and Berg, P., J. Mol. Appl. Genet., 1: 327 (1982)). The selectable marker gene can be either linked to the DNA gene sequences to be expressed, or introduced into the same cell by co-transfection (Wigler, M. et al., Cell, 16: 77 (1979)). A second class of vectors utilizes DNA elements which confer autonomously replicating capabilities to an extrachromosomal plasmid. These vectors can be derived from animal viruses, such as bovine papillomavirus (Sarver, N. et al., Proc. Natl. Acad. Sci., USA, 79: 7147 (1982)), polyoma virus (Deans, R. J. et al., Proc. Natl. Acad. Sci., USA, 81: 1292 (1984)), or SV40 virus (Lusky, M. and Botchan, M., Nature, 293: 79 (1981)).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama, H. and Berg, P., Mol. Cell. Biol., 3: 280 (1983); Cepko, C. L. et al., Cell, 37: 1053 (1984); and Kaufman, R. J., Proc. Natl. Acad. Sci., USA, 82: 689 (1985).

In certain embodiments, an anti-CD200 antibody may be a blocking or agonistic. As used herein, a blocking antibody is one that blocks the interaction between CD200 and CD200R. An agonistic antibody is one that enhances the interaction between CD200 and CD200R. Thus in certain embodiments, an anti-CD200 antibody is either a blocking or agonistic murine, chimeric, humanized, human or de-immunized antibody.

The CD200 antibodies and polypeptides and/or antibodies utilized in the present disclosure are especially indicated for diagnostic and therapeutic applications as described herein. Accordingly CD200 antibodies and anti-CD200 antibodies and variants thereof may be used in therapies, including combination therapies, in the diagnosis and prognosis of disease, as well as in the monitoring of disease progression.

In the therapeutic embodiments of the present disclosure, bispecific antibodies are contemplated. Bispecific antibodies are monoclonal, preferably human or humanized, antibodies that have binding specificities for at least two different antigens. In the present case, one of the binding specificities is for the CD200 antigen on a cell (such as, e.g., an immune cell), the other one is for any other antigen, and preferably for a cell-surface protein or receptor or receptor subunit.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Antibody variable domains with the desired binding specificities (antibody-antigen combining sites) can be fused to immunoglobulin constant domain sequences. The fusion preferably is with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, for example, Suresh et al., Methods in Enzymology, 121:210 (1986); WO 96/27011; Brennan et al., Science 229:81 (1985); Shalaby et al., J. Exp. Med. 175:217-225 (1992); Kostelny et al., J. Immunol. 148(5):1547-1553 (1992); Hollinger et al., Proc. Natl. Acad. Sci. USA 90:6444-6448 (1993); Gruber et al., J. Immunol. 152:5368 (1994); and Tutt et al., J. Immunol. 147:60 (1991). Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (scFv) dimers has also been reported. See Gruber et al., J. Immunol., 152:5368 (1994). Alternatively, the antibodies can be "linear antibodies" as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

III. Methods of Treating Patients with Autoimmune Disorders

In certain aspects, the disclosure relates to treating patients with autoimmune disorders with a therapy comprising an anti-CD200 antibody or antigen-binding fragment thereof. In certain aspects, the disclosure relates to treating patients with an unwanted immune response with a therapy comprising an anti-CD200 antibody or antigen-binding fragment thereof. The antibody may be antagonistic, agonistic or a non-blocking antibody and may be a murine, chimeric, humanized, human or de-immunized anti-CD200 antibody. Thus, methods of treating patients with autoimmune disorders or an unwanted immune response may comprise any of the CD200 antibodies as set forth in the present disclosure.

In certain embodiments, anti-CD200 antibodies may be used for depleting any type of cell that expresses CD200 on its surface, including for example, immune cells such as T-cells, B-cells, and dendritic cells. In one embodiment, anti-CD200 antibodies may be useful for targeted destruction of immune cells involved in an unwanted immune response.

In certain aspects, the disclosure relates to treating patients with autoimmune disorders or an unwanted immune response with a therapy comprising an anti-CD200 antibody or antigen-binding fragment thereof that blocks the production of auto-antibodies. In certain embodiments, said auto-antibodies are selected from IgG1, IgG2, IgG3, IgG4, IgM, IgA1, IgA2, IgA, IgD, and/or IgE immunoglobulins. In certain embodiments, said antibody may be any antibody or antigen-binding fragment thereof of the application. In certain embodiments, an antibody or antigen-binding fragment thereof of the application does not block the production of auto-antibodies.

In certain aspects, the disclosure relates to treating patients with autoimmune disorders or an unwanted immune response with a therapy comprising an anti-CD200 antibody or antigen-binding fragment thereof that modulates expression of cytokines in said patient. In certain embodiments, said antibody or antigen-binding fragment thereof enhances production of a cytokine in said patient selected from the group consisting of: IL-12, IL-10 and IL-4. In certain embodiments, said antibody or antigen-binding fragment thereof modulates production of a cytokine in said patient selected from the group consisting of: IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, and IL-33. In certain embodiments, said antibody may be any antibody or antigen-binding fragment thereof of the application.

An unwanted immune response may be, for example, immune responses associated with an autoimmune disorder, transplants, allergies, or inflammatory disorders. Exemplary autoimmune diseases and disorders that may be treated with the anti-CD200 antibodies provided herein include, for example, inflammatory responses such as inflammatory skin diseases including psoriasis and dermatitis (e.g. atopic dermatitis); dermatomyositis; systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Bechet disease; giant cell arteritis; immune complex nephritis; IgA nephropathy; IgM polyneuropathies; immune thrombocytopenic purpura (ITP) or autoimmune thrombocytopenia and autoimmune hemolytic diseases, Hashimoto's thyroiditis, Wegener's granulomatosis, cold agglutinin disease associated with indolent lymphoma, acquired factor VIII inhibitors disease, etc.

Therapies comprising CD200 antibodies may be administered to patients in combination therapies. Accordingly, targeted killing of certain populations of immune cells for treating or preventing autoimmune disorders, enhancing or extending transplant survival, treating or preventing allergies, or treating or preventing inflammatory disorders, may be administered as part of a combination therapy. For example, a patient receiving a first therapy comprising a CD200 antibody (e.g., an anti-CD200 antibody described herein) may also be given a second therapy. The CD200 antibody may be given simultaneously with the second therapy. Alternatively, the CD200 antibody may be given prior to or following the second therapy. Second therapies include but are not limited to anti-inflammatory agents, immunosuppressive agents, and/or anti-infective agents.

Combination therapies of the present disclosure include, for example, a CD200 antibody as described herein administered concurrently or sequentially in series with steroids, anti-malarials, aspirin, non-steroidal anti-inflammatory drugs, immunosuppressants, or cytotoxic drugs. Included are corticosteroids (e.g. prednisone, dexamethasone, and prednisolone), methotrexate, methylprednisolone, macrolide immunosuppressants (e.g. sirolimus and tacrolimus), mitotic inhibitors (e.g. azathioprine, cyclophosphamide, and methotrexate), fungal metabolites that inhibit the activity of T lymphocytes (e.g. cyclosporine), mycophenolate mofetil, glatiramer acetate, and cytotoxic and DNA-damaging agents (e.g. chlorambucil). For autoimmune disorders anti-CD200 therapy may be combined with antibody treatments including daclizumab, a genetically engineered human IgG1 monoclonal antibody that binds specifically to the α-chain of the interleukin-2 receptor, as well as various other antibodies targeting immune cells or other cells. Such combination therapies may be useful in the treatment of type 1 diabetes, rheumatoid arthritis, lupus, and idiopathic thrombocytopenic purpura, and other autoimmune indications. The disclosure also relates to therapies for autoimmune disorders and for transplant patients comprising a CD200 antibody (such as, for example, the antibodies and variants thereof described in the present disclosure) conjugated to one or more agent.

IV. Modes of Administration and Formulations

The route of antibody administration of the antibodies of the present disclosure (whether the pure antibody, a labeled antibody, an antibody fused to a toxin, etc.) is in accord with known methods, e.g., injection or infusion by intravenous, intraperitoneal, intracerebral, intramuscular, subcutaneous, intraocular, intraarterial, intrathecal, inhalation or intralesional routes, or by sustained release systems. The antibody is preferably administered continuously by infusion or by bolus injection. One may administer the antibodies in a local or systemic manner.

The present antibodies may be prepared in a mixture with a pharmaceutically acceptable carrier. Techniques for formulation and administration of the compounds of the instant application may be found in "Remington's Pharmaceutical Sciences," Mack Publishing Co., Easton, Pa., latest edition. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, substantially pyrogen-free and in a parenterally acceptable solution having due regard for pH, isotonicity, and stability. For example, a pharmaceutical preparation is substantially free of pyrogenic materials so as to be suitable for administration as a human therapeutic. These conditions are known to those skilled in the art.

In certain embodiments, any antibody or antigen-binding fragment thereof of the application is administered acutely to said mammal. In certain embodiments, said antibody or antigen-binding fragment thereof is administered for at least one month to said mammal. In certain embodiments, said antibody or antigen-binding fragment thereof is administered for at least 2, 3, 4, 5, 6, 7, 8, 9, 10, or 11 months to said mammal. In certain embodiments, said antibody or antigen-binding fragment thereof is administered for at least one year to said mammal. In certain embodiments, said antibody or antigen-binding fragment thereof is administered for at least 2, 3, 4, 5, 6, 7, 8, 9, or 10 years to said mammal. In certain embodiments, said antibody or antigen-binding fragment thereof is administered chronically to said mammal, i.e., recurrently for at least 14 days, 28 days, 3 months, 6 months, 1 year, 5 years, or longer. In certain embodiments, said antibody or antigen-binding fragment thereof is administered to said mammal for the remainder of its life.

Pharmaceutical compositions suitable for use include compositions wherein one or more of the present antibodies are contained in an amount effective to achieve their intended purpose. More specifically, a therapeutically effective amount means an amount of antibody effective to prevent, alleviate or ameliorate symptoms of disease or prolong the survival of the subject being treated. Determination of a therapeutically effective amount is well within the capability of those skilled in the art, especially in light of the detailed disclosure provided herein. Therapeutically effective dosages may be determined by using in vitro and in vivo methods.

EXEMPLIFICATION

Example 1

Materials and Methods

Induction and Evaluation of Collagen Induced Arthritis (CIA)
Preparation of Reagents:
1. Preparation of BCII: (Bovine type II Collagen from Elastin Products).
BCII is reconstituted by stirring overnight in cold room in 0.01 M Acetic Acid at a concentration of 4 mg/mL.
2. Preparation of Complete Freund's Adjuvant (CFA) H37Ra (Difco):
10 mg *Mycobacterium tuberculosis* is added to 10 ml Complete Freund's Adjuvant which contains 10 mg *Mycobacterium tuberculosis* so that the final concentration for *Mycobacterium tuberculosis* is 2 mg/mL. CFA is stirred overnight at 4° C. overnight.
3. Preparation of emulsion (4° C.):
1:1 ratio of 4 mg/mL BCII and CFA with *Mycobacterium tuberculosis* (2 mg/mL) 100 μL emulsion=200 μg BCII+100 μg CFA-M.T H37Ra 4. Intradermal injection:
Inject 150 μL of emulsion intradermally at the base of the mouse tail.
Mice will be re-immunized 21 days after the first immunization following the identical protocol.
Evaluation of CIA:
The severity of arthritis was determined by scoring and measuring the front paws, hind paws, elbow and knee joints with a caliper.
  1. Arthritis scores:
     0=No paw swelling
     1=mild/moderate visible erythema and swelling
     2=severe erythema and swelling affecting an entire paw or joint
     3=deformed paw or joint with ankylosis
  The parameters for determining the above scores were:

| Paw | Elbow | Knee |
|---|---|---|
| 0 - Normal | 0 - <3.3 mm | 0 - <4 mm |
| 1 - R/SW < 2.2 mm | 1 - SW 3.4-3.5 mm | 1 - SW 4.3-4.5 mm |
| 2 - R/SW 2.2-3.2 mm | 2 - R/SW 3.5-3.6 mm | 2 - R/SW 4.5-5 mm |
| 3 - R/SW > 3.2 mm | 3 - R/SW > 3.6 mm | 3 - R/SW > 5 mm |

R/SW—redness and swelling
  2. The degree of swelling was visually examined and measured with a caliper at the following time points:
     Time: 1) before immunization.
        2) once/day starting from day 21 to day 42.
A Total Arthritic Score was calculated by adding the measurements for each paw, elbow and knee (total of 8 measurements per mouse thus yielding a maximal score of 24).
Serum Collection Time:
  1. Before immunization
  2. day 14 and day 28 for prevention treatment group, day 31 for therapeutic treatment group.
  3. day 42 after first immunization
  4. Serum anti-collagen antibodies (B cell response) were measured at the times indicated in FIGS. 2 and 3B.
  5. Spleen cells for cytokine measurement were taken when the animals were sacrificed.
Histological Examination: Day 42 after First Immunization
Protocol for Intracellular Staining for Cytokine Detection (Splenocytes)
1. Collect animal spleen in plain HBSS or PBS on ice;
2. Homogenize the spleen to collect splenocytes in 5-10 mL of plain HBSS or PBS, spin down the cells by 1,250 rpm×5 min, rm. tp.;
3. Discard supernatant, re-suspend the cell pellet by vortex, add 5-10 mL of ACK cell lysis buffer (155 mM $NH_4Cl$, 10 mM $KHCO_3$, 0.1 mM $Na_2EDTA$ $2H_2O$) on to the cells for 3 min. at rm. tp.;
4. Add FACS Washing/Staining Buffer (2% FBS/HBSS+0.02% Sodium Azide) fill to the top of the tube and spin down the cells by 1,250 rpm×5 min, rm. tp.;
5. Repeat wash twice;
6. Count the cells and then distribute $1.0×10^6$ cells/50 μL/well in to the 96 well U-bottom plate;
7. Add antibodies (0.1 μg/well=$1.0×10^6$ cells) into the wells according to the staining plan, if both antibodies for the double staining are for the cell surface markers these can be added together in this step, for 30-60 min. 4° C. in dark;
8. Repeat wash 3 times using FACS washing/staining buffer, 250 μL/well;
9. Add CytoFix buffer (BD Pharmingen Kit) 250 μL/well for 30 min. 4° C. in dark;

10. Wash wells with CytoPerm/CytoWash 3 times;
11. Re-suspend cells with 50 μL/well of CytoPerm/CytoWash buffer, add antibodies against cytokines (0.1 μg/well=1.0× $10^6$ cells), incubate for 30-60 min. 4° C. in dark;
12. Repeat wash with FACS washing buffer twice, see above #8, wash plate once with plain PBS;
Re-suspend wells to add 250 μL/well of plain PBS, transfer the cells into the FACS tube. The samples are now ready for running the FACS.

Example 2

Evaluation of Anti-CD200 on Arthritis Animal Model

Administration of anti-CD200 antibody was performed in mice to test: 1) whether administration of anti-CD200 antibody prevents the development of arthritis and 2) whether administration of anti-CD200 antibody reduces the severity of existing arthritis. A collagen induced arthritis (CIA) mouse model was used (mouse strain: DBA/1LacJ from Jackson Labs, male, 8 to 12 weeks old).

The anti-CD200 mAb used was OX90mG2a, a chimeric antibody derived from OX90, a rat anti-mouse CD200 mAb obtained as a hybridoma from the European Collection of Cell Cultures (ECACC No. 03062502; see Hoek et al., Science 290:1768-1771 (2000)). The rat antibody was genetically modified to contain the rat heavy chain variable regions fused to a murine IgG2a constant region and the rat light chain variable region fused to a murine kappa constant region. An isotype matched control mAb, r12B4 was used as a control.

A) Prevention of Arthritis

Ten DBA/1LacJ mice were administered a 5 mg/kg dose of either anti-CD200 or isotype-matched control mAb by i.p. injection from day 1 to day 7 and day 21 to day 25 after initial BCII immunization on day 1. An additional 10 mice were treated again at day 21 to day 25 and were terminated at day 42. Mice were bled at day 14 to measure antibody response.

Figure 2:
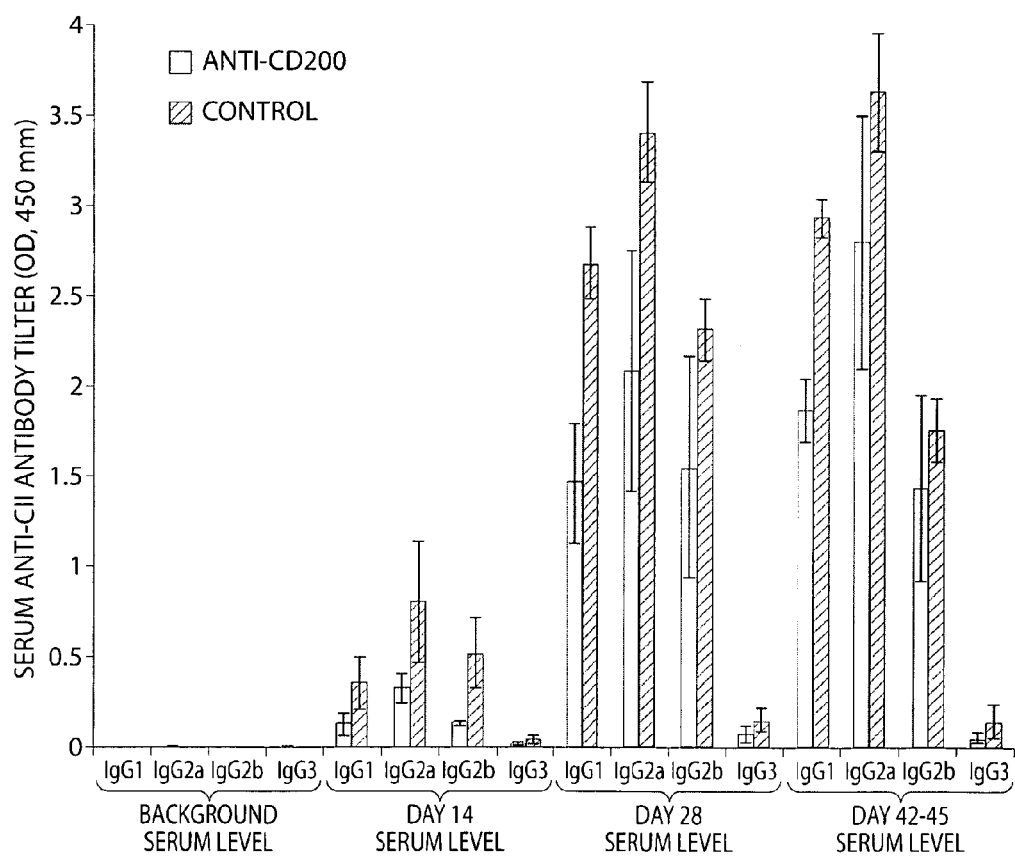
FIG. 2 shows anti-CD200 treatment blocks the production of anti-collagen antibody production. Serum levels and subtypes of anti-BCII Abs were evaluated for the indicated treatment groups. Data are presented as mean±SEM.

As seen in FIG. 1, anti-CD200 treatment reduces the severity of collagen induced arthritis (FIG. 1). Anti-CD200 treatment also inhibits the production of anti-collagen antibody production (FIG. 2). Serum levels and subtypes of anti-BCII Abs were evaluated for the indicated treatment groups. DBA/1LacJ mice were i.p. injected with either anti-CD200 or isotype-matched control mAb from day 1 to day 7 and day 21 to day 25 and bled at pre-immunization, day 14, day 28 and day 42 to day 45 after initial BCII immunization on day 1.

B) Amelioration of Established Arthritis

Figure 3A:
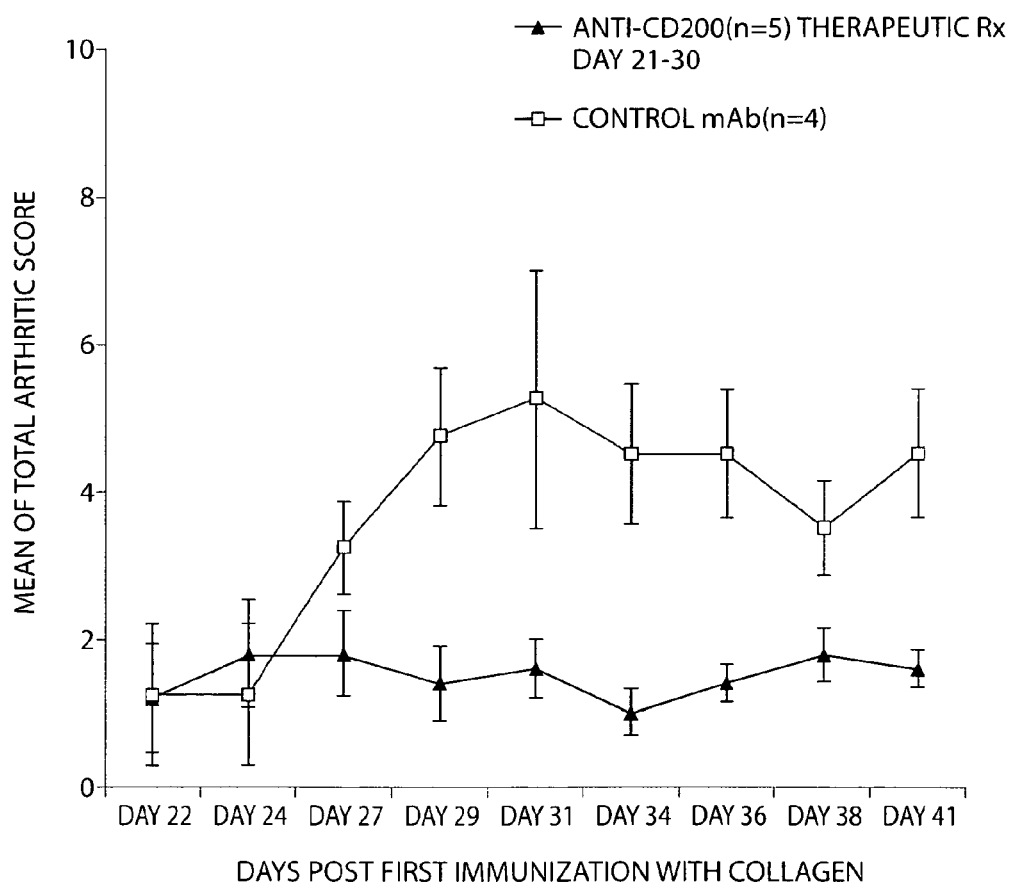
FIGS. 3A-3B show anti-CD200 treatment can ameliorate established joint inflammation independent of the effect on autoantibody production. A) DBA/1LacJ mice were administered 5 mg/kg dose of either anti-CD200 or isotype-matched control mAb by i.p. injection on day 21 to day 30 after initial BCII immunization on day 1. B) Serum levels and subtypes of anti-BCII Abs were evaluated for the indicated treatment groups. Data are presented as mean±SEM.
Figure 3B:
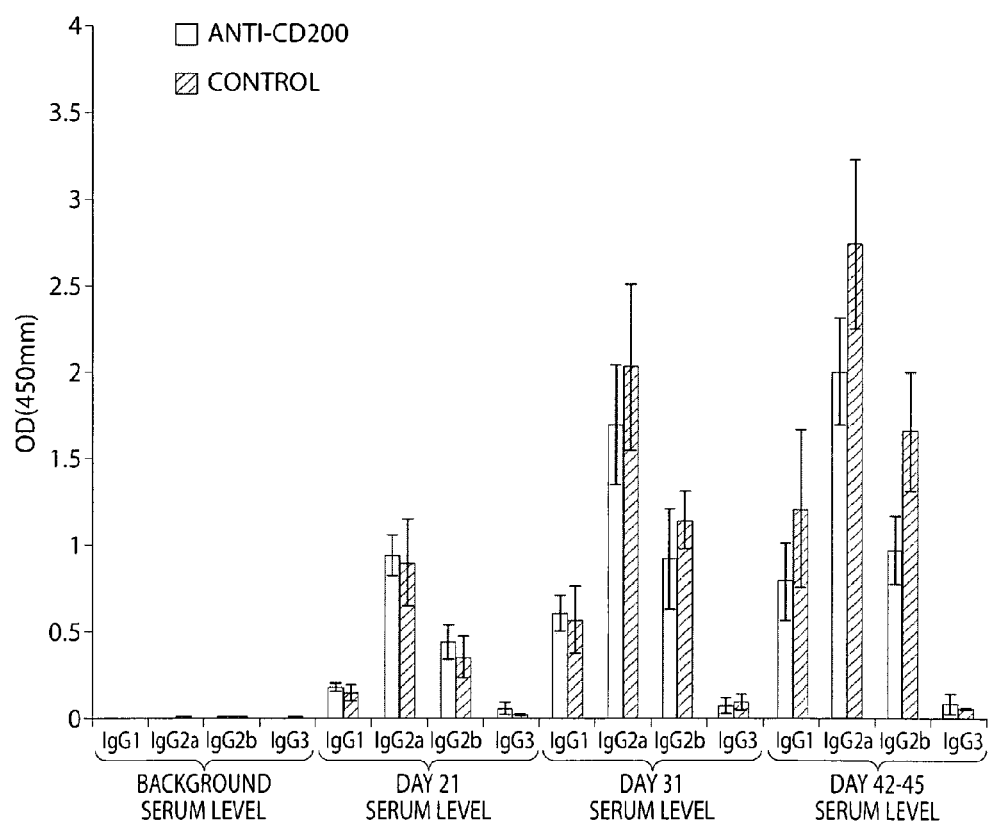

DBA/1LacJ mice were administered a 5 mg/kg dose of either anti-CD200 or isotype-matched control mAb by i.p. injection on day 21 to day 30 after initial BCII immunization on day 1. Serum levels and subtypes of anti-BCII Abs were evaluated for the indicated treatment groups. DBA/1 LacJ mice were i.p. injected with either anti-CD200 or isotype-matched control mAb from day 21 to day 30 and bled at pre-immunization, day 14, day 28 and day 42 to day 45 after initial BCII immunization on day 1. As shown in FIGS. 3A-B, anti-CD200 treatment can ameliorate established joint inflammation independently of the effect on autoantibody production.

Figure 4A:
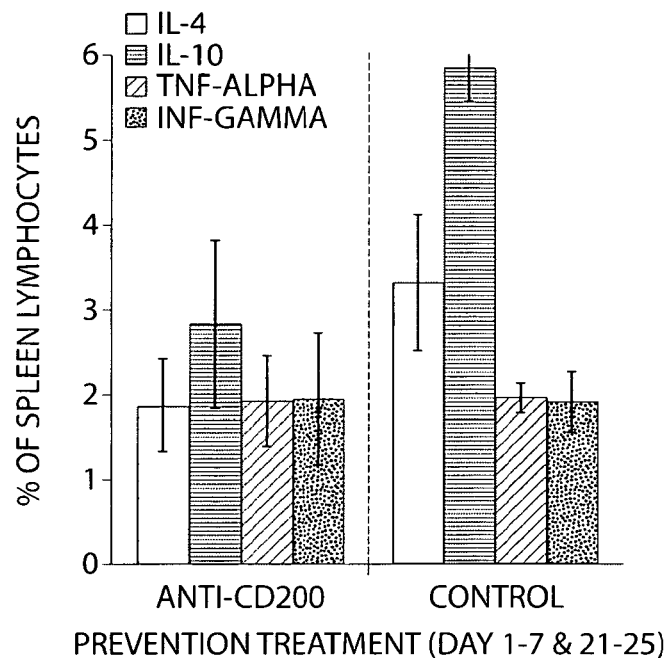
FIGS. 4A-4B show anti-CD200 treatment affects splenic cytokine profiles when administered at various time points relative to collagen immunization of DBA/1 mice. A) Spleen cells were isolated from BCII immunized DBA/1LacJ mice, which were treated with either anti-CD200 or isotype-matched control mAb from day 1 to day 7 and day 21 to day 25 after initial BCII immunization on day 1. B) Spleen cells were isolated from BCII immunized DBA/1LacJ mice, which were treated with either anti-CD200 or isotype-matched control mAb from day 21 to day 30 after initial BCII immunization on day 1. Data are presented as mean±SEM.
Figure 4B:
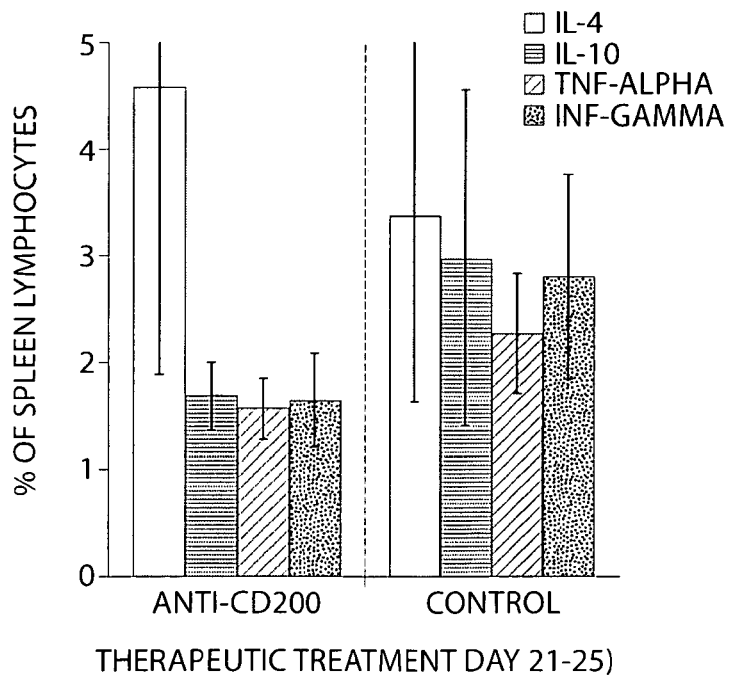

Anti-CD200 treatment affects splenic cytokine profiles when administered at various time points relative to collagen immunization of DBA/1 mice (FIGS. 4A-4B). Spleen cells were isolated from BCII immunized DBA/1LacJ mice, which were treated with either anti-CD200 or isotype-matched control mAb from day 1 to day 7 and day 21 to day 25 after initial BCII immunization on day 1. The percentage of IL-4, IL-10, TNF-α and INF-γ producing cells were analyzed by intracellular staining with anti-IL-4, anti-IL-10, anti-TNF-α, anti-INF-γ or with isotype-matched control IgG1 Ab. Spleen cells were isolated from BCII immunized DBA/1LadJ mice, which were treated with either anti-CD200 or isotype-matched control mAb from day 21 to day 30 after initial BCII immunization on day 1. The percentage of IL-4, IL-10, TNF-α and INF-γ producing cells were analyzed by intracellular staining with anti-IL-4, anti-IL-10, anti-TNF-α, anti-INF-γ or with isotype-matched control IgG1 Ab.

Figure 5:
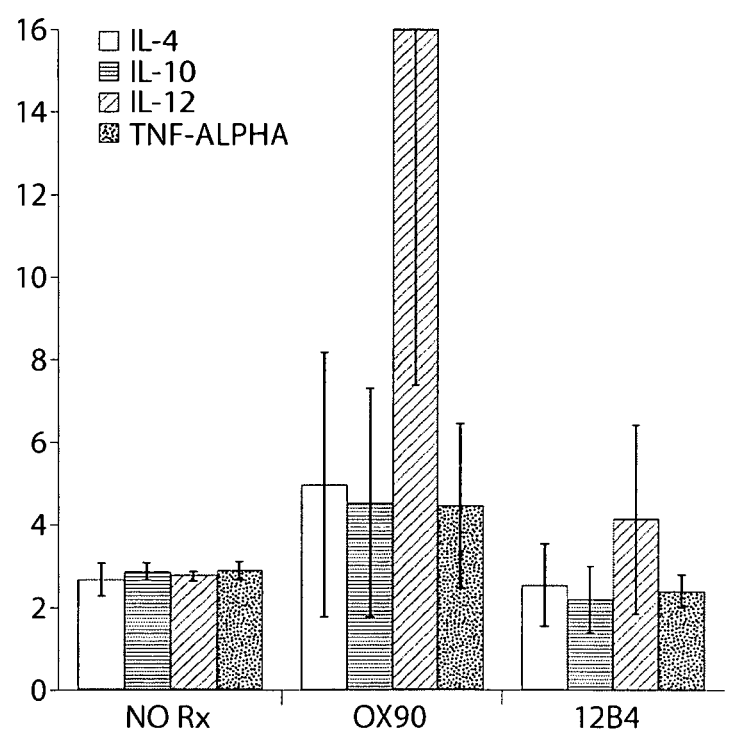
FIG. 5 shows the effect of alteration of cytokine profile after anti-CD200 treatment in an allogenic immune response, where BALB/c mice were immunized with C57B/c spleen cells. Data are presented as mean±SEM.

The effect of alteration of cytokine profile after anti-CD200 treatment was further demonstrated in an allogenic immune response, where BALB/c mice were immunized with C57B/c spleen cells (FIG. 5).

It will be understood that various modifications may be made to the embodiments disclosed herein. For example, as those skilled in the art will appreciate, the specific sequences described herein can be altered slightly without necessarily adversely affecting the functionality of the polypeptide, antibody or antibody fragment used in binding OX-2/CD200. For instance, substitutions of single or multiple amino acids in the antibody sequence can frequently be made without destroying the functionality of the antibody or fragment. Thus, it should be understood that polypeptides or antibodies having a degree of identity greater than 70% to the specific antibodies described herein are within the scope of this disclosure. In particularly useful embodiments, antibodies having an identity greater than about 80% to the specific antibodies described herein are contemplated. In other useful embodiments, antibodies having an identity greater than about 90% to the specific antibodies described herein are contemplated. Therefore, the above description should not be construed as limiting, but merely as exemplifications of preferred embodiments. Those skilled in the art will envision other modifications within the scope and spirit of this disclosure.

REFERENCES

The following references are incorporated herein by reference to more fully describe the state of the art to which the present invention pertains. Any inconsistency between these publications below or those incorporated by reference above and the present disclosure shall be resolved in favor of the present disclosure.

1) Agarwal, et al. (2003). Disregulated expression of the Th2 cytokine gene in patients with intraoral squamous cell carcinoma. Immunol Invest 32:17-30.
2) Almasri, N M et al. (1992). Am J Hematol 40: 259-263.
3) Contasta, et al. (2003). Passage from normal mucosa to adenoma and colon cancer: alteration of normal sCD30 mechanisms regulating TH1/TH2 cell functions. Cancer Biother Radiopharm 18:549-557.
4) Gorczynski, et al. (1998). Increased expression of the novel molecule OX-2 is involved in prolongation of murine renal allograft survival. Transplantation 65:1106-1114.
5) Gorczynski, et al. (2001). Evidence of a role for CD200 in regulation of immune rejection of leukaemic tumour cells in C57BL/6 mice. Clin Exp Immunol 126:220-229.
6) Hainsworth, J D (2000). Oncologist 2000; 5(5):376-84.
7) Inagawa, et al. (1998). Mechanisms by which chemotherapeutic agents augment the antitumor effects of tumor necrosis factor: involvement of the pattern shift of cytokines from Th2 to Th1 in tumor lesions. Anticancer Res 18:3957-3964.

8) Ito, et al. (1999). Lung carcinoma: analysis of T helper type 1 and 2 cells and T cytotoxic type 1 and 2 cells by intracellular cytokine detection with flow cytometry. Cancer 85:2359-2367.
9) Kiani, et al. (2003). Normal intrinsic Th1/Th2 balance in patients with chronic phase chronic myeloid leukemia not treated with interferon-alpha or imatinib. Haematologica 88:754-761.
10) Lauerova, et al. (2002). Malignant melanoma associates with Th1/Th2 imbalance that coincides with disease progression and immunotherapy response. Neoplasma 49:159-166.
11) Maggio, et al. (2002). Chemokines, cytokines and their receptors in Hodgkin's lymphoma cell lines and tissues. Ann Oncol 13 Suppl 1:52-56.
12) Nilsson, K (1992). Burn Cell. 5(1):25-41.
13) Podhorecka, et al. (2002). T type 1/type 2 subsets balance in B-cell chronic lymphocytic leukemia—the three-color flow cytometry analysis. Leuk Res 26:657-660.
14) Pu, Q Q and Bezwoda, W (2000). Anticancer Res. 20(4): 2569-78.
15) Smyth, et al. (2003). Renal cell carcinoma induces prostaglandin E2 and T-helper type 2 cytokine production in peripheral blood mononuclear cells. Ann Surg Oncol 10:455-462.
16) Tatsumi, et al. (2002). Disease-associated bias in T helper type 1 (Th1)/Th2 CD4(+) T cell responses against MAGE-6 in HLA-DRB10401(+) patients with renal cell carcinoma or melanoma. J Exp Med 196:619-628.
17) Walls et al. (1989). Int. J. Cancer 44846-853.
18) Winter, et al. (2003). Tumour-induced polarization of tumour vaccine-draining lymph node T cells to a type 1 cytokine profile predicts inherent strong immunogenicity of the tumour and correlates with therapeutic efficacy in adoptive transfer studies. Immunology 108:409-419.
19) Cameron, C. M., J. W. Barrett, L. Liu, A. R. Lucas, and G. McFadden. 2005. Myxoma virus M141R expresses a viral CD200 (vOX-2) that is responsible for down-regulation of macrophage and T-cell activation in vivo. J Virol 79:6052.
20) Foster-Cuevas, M., G. J. Wright, M. J. Puklavec, M. H. Brown, and A. N. Barclay. 2004. Human herpesvirus 8 K14 protein mimics CD200 in down-regulating macrophage activation through CD200 receptor. J Virol 78:7667.
21) Nicholas, J. 2003. Human herpesvirus-8-encoded signalling ligands and receptors. J Biomed Sci 10:475.
22) Shiratori, I., M. Yamaguchi, M. Suzukawa, K. Yamamoto, L. L. Lanier, T. Saito, and H. Arase. 2005. Down-regulation of basophil function by human CD200 and human herpesvirus-8 CD200. *J Immunol* 175:4441.
23) Voigt, S., G. R. Sandford, G. S. Hayward, and W. H. Burns. 2005. The English strain of rat cytomegalovirus (CMV) contains a novel captured CD200 (vOX2) gene and a spliced CC chemokine upstream from the major immediate-early region: further evidence for a separate evolutionary lineage from that of rat CMV Maastricht. J Gen Virol 86:263.
24) Zhang, J., J. Wang, C. Wood, D. Xu, and L. Zhang. 2005. Kaposi's sarcoma-associated herpesvirus/human herpesvirus 8 replication and transcription activator regulates viral and cellular genes via interferon-stimulated response elements. J Virol 79:5640.

The invention claimed is:

1. A method for treating a patient who has established rheumatoid arthritis, said method comprising administering to said patient a therapeutically effective amount of an anti-CD200 antibody or antigen-binding fragment thereof, wherein the anti-CD200 antibody or antigen-binding fragment thereof inhibits interaction between CD200 and CD200R.

2. The method of claim 1, wherein said anti-CD200 antibody or antigen-binding fragment thereof is a monoclonal antibody or antigen-binding fragment thereof.

3. The method of claim 1, wherein said anti-CD200 antibody or antigen-binding fragment thereof is administered for at least one month to said patient.

4. The method of claim 1, wherein said anti-CD200 antibody or antigen-binding fragment thereof is administered for at least one year to said patient.

5. The method of claim 1, wherein said anti-CD200 antibody or antigen-binding fragment thereof is administered chronically to said patient.

6. The method of claim 1, wherein said anti-CD200 antibody or antigen-binding fragment thereof is administered systemically to said patient.

7. The method of claim 1, wherein said anti-CD200 antibody or antigen-binding fragment thereof is administered locally to said patient.

8. The method of claim 1, further comprising administering a second agent or therapy.

9. The method of claim 8, wherein said second agent is administered either sequentially or simultaneously with said anti-CD200 antibody or antigen-binding fragment thereof.

10. The method of claim 1, wherein said anti-CD200 antibody or antigen-binding fragment thereof enhances production of a cytokine in said patient selected from the group consisting of: IL-12, IL-10 and IL-4.

11. The method of claim 1, wherein said anti-CD200 antibody or antigen-binding fragment thereof is further conjugated to one or more agents.

* * * * *